(12) United States Patent
Klich et al.

(10) Patent No.: US 6,812,331 B2
(45) Date of Patent: Nov. 2, 2004

(54) AROMATIC DERIVATIVES SUBSTITUTED BY A RIBOSE, THEIR PREPARATION PROCESS AND THEIR USE AS MEDICAMENTS

(75) Inventors: Michel Klich, Villemomble (FR); Patrick Laurin, Montreuil (FR); Branislav Musicki, Paris (FR); Laurent Schio, Bondy (FR)

(73) Assignee: Aventis Pharma S.A. (FR)

( * ) Notice: Subject to any disclaimer, the term of this patent is extended or adjusted under 35 U.S.C. 154(b) by 390 days.

(21) Appl. No.: 09/875,860

(22) Filed: Jun. 7, 2001

(65) Prior Publication Data
US 2002/0010322 A1 Jan. 24, 2002

Related U.S. Application Data

(62) Division of application No. 09/202,218, filed as application No. PCT/FR97/01022 on Jun. 10, 1997.

(51) Int. Cl.[7] .................. C07H 17/00; C07H 17/04; A61K 31/70
(52) U.S. Cl. .................. 536/16.8; 514/27; 514/28; 536/4.1; 540/544; 540/552
(58) Field of Search .................. 514/27, 28; 536/4, 536/6.8; 540/544, 552

(56) References Cited

U.S. PATENT DOCUMENTS 6,420,538 B1 * 7/2002 Haesslein et al. .............. 536/8

* cited by examiner

Primary Examiner—Howard V Owens
(74) Attorney, Agent, or Firm—Muserlian, Lucas and Lucas

(57) ABSTRACT

A subject of the invention is the compounds of formula (I):

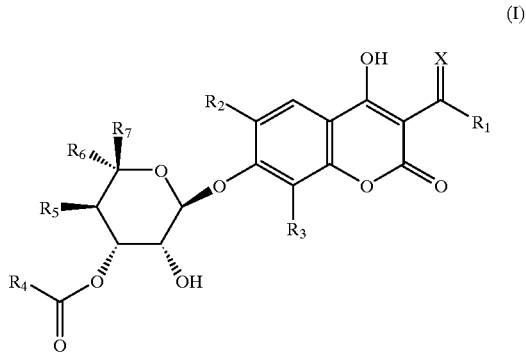

(I)

$R_1$=H, OH, alkyl, alkenyl or alkynyl optionally substituted or alkoxy,
$R_2$=H, Hal,
$R_3$=H, alkyl, Hal,

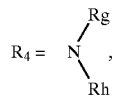

Rg and Rh: H, alkyl, aryl heterocycle,
$R_5$=H or O-alkyl,
$R_6$=alkyl or $CH_2$—O-alkyl,
$R_7$=H or alkyl.

The compounds of formula (I) have antibiotic properties.

1 Claim, No Drawings

AROMATIC DERIVATIVES SUBSTITUTED BY A RIBOSE, THEIR PREPARATION PROCESS AND THEIR USE AS MEDICAMENTS

This application is a division of U.S. patent application Ser. No. 09/202,218 filed Dec. 21, 1998 which is a 371 of PCT/FR97/01022 filed Jun. 10, 1997.

The present invention relates to new aromatic derivatives, substituted by a ribose, their preparation process and their use as medicaments.

A subject of the invention is the compounds of formula (I):

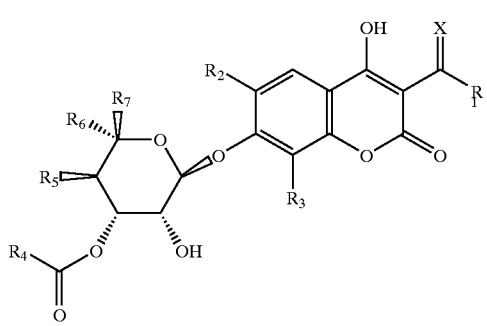

in which:

$R_1$ represents a hydrogen atom, a hydroxyl radical, analkyl, alkenyl or alkynyl radical optionally interrupted by an oxygen, sulphur or nitrogen atom, containing up to 12 carbon atoms, linear, branched or cyclic, optionally substituted by one or more halogen atoms, one or more OH,

C≡N, $NO_2$,

radicals, in which Ra and Rb, identical or different, represent a hydrogen atom, an alkyl radical containing up to 8 carbon atoms, or Ra and Rb form with the nitrogen atom to which they are linked a heterocycle optionally containing another heteroatom chosen from nitrogen, sulphur or oxygen, or $R_1$ represents an alkoxy radical containing up to 8 carbon atoms, optionally substituted by one or more of the substituents indicated above, or $R_1$ represents an NRcRd radical in which Rc and Rd, identical or different, represent a hydrogen atom or an alkyl radical optionally interrupted by an oxygen, sulphur or nitrogen atom, containing up to 12 carbon atoms, optionally substituted by one or more of the substituents indicated above, or $R_c$ and $R_d$ form together with the nitrogen atom to which they are linked a heterocycle optionally containing another heteroatom chosen from nitrogen, sulphur or oxygen, X represents an oxygen atom, or an N-Nalk$_1$ or NOalk$_2$ radical in which alk$_1$ and alk$_2$ represent an alkyl radical containing up to 12 carbon atoms optionally substituted by one or more halogen atoms, by one or more

radicals in which Re and Rf, identical to or different from each other represent a hydrogen atom, an alkyl radical containing up to 8 carbon atoms, optionally substituted, or Re and Rf are able to form together with the nitrogen atom to which they are joined a heterocycle which in addition is able to contain an oxygen, sulphur atom and another nitrogen atom, $R_2$ represents a hydrogen atom or a halogen atom, $R_3$ represents a hydrogen atom, an alkyl radical containing up to 8 carbon atoms or a halogen atom, $R_4$ represents an

radical in which Rg and Rh, identical to or different from each other, represent a hydrogen atom, a linear, branched, cyclic alkyl radical containing up to 8 carbon atoms, an optionally substituted aryl or heteroaryl radical, or Rg and Rh form together with the nitrogen atom to which they are linked a heterocycle which is able to contain in addition an oxygen atom, sulphur atom and another nitrogen atom, or $R_4$ represents an aryl or heteroaryl radical optionally substituted by one or more halogen atoms, one or more hydroxyl radicals, one or more alkyl or alkoxy radicals containing up to 8 carbon atoms, $R_5$ represents a hydrogen atom, an O-alkyl radical containing up to 4 carbon atoms, $R_6$ an alkyl or CH$_2$—O-alkyl radical, in which alkyl represents an alkyl radical containing up to 8 carbon atoms, $R_7$ represents a hydrogen atom or an alkyl radical containing up to 8 carbon atoms, as well as their salts.

As examples of salts there can be mentioned sodium, potassium, lithium, calcium or magnesium salts, the salts obtained with nitrogenous bases such as trimethylamine, triethylamine, methylamine, propylamine, N,N-dimethylethanol-amine and tris (hydroxymethyl) methylamine.

As examples of salts there can also be mentioned the salts formed with the following acids: acetic, propionic, trifluoroacetic, maleic, tartaric, methanesulphonic, benzenesulphonic, p-toluenesulphonic, hydrochloric, hydrobromic, hydroiodic, sulphuric, phosphoric and especially stearic, ethylsuccinic or laurylsulphonic acids.

In the definition of the substituents:

the alkyl, alkenyl or alkynyl radical is preferably a methyl, ethyl, propyl, isopropyl, n-butyl, isobutyl, terbutyl, decyl or dodecyl, vinyl, allyl, ethynyl, propynyl, cyclobutyl, cyclopentyl or cyclohexyl radical, the halogen is preferably fluorine or chlorine, or bromine, the aryl radical is preferably the phenyl radical, the heterocyclic radical is preferably the pyrrolyl, pyrrolidinyl, pyridyl, pyrazinyl, pyrimidyl, piperidinyl, piperazinyl, quinuclidinyl, oxazolyl, isoxazolyl, morpholinyl, indolyl, imidazolyl, benzimidazolyl, triazolyl, thiazolyl, azetidinyl, aziridinyl radical.

Among the preferred compounds of the invention, there can be mentioned the compounds in which $R_2$ represents a hydrogen atom, those in which $R_3$ represents a methyl radical, those in which $R_6$ represents a methyl radical, those in which $R_7$ represents a hydrogen atom or a methyl radical and those in which $R_5$ represents an $OCH_3$ radical.

Quite especially a subject of the invention is the compounds of formula (I), in which $R_4$ represents a

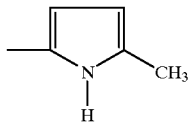

radical, or also those in which $R_4$ represents an NH-cyclopropyl radical.

Among the compounds of the invention, there can be quite particularly mentioned the compounds of formula (I) in which X represents an oxygen atom, those in which X represents an NOR radical, R representing an alkyl radical, optionally substituted by one or more halogen atoms and optionally interrupted by an oxygen, nitrogen, sulphur atom and optionally carrying an optionally substituted heterocyclic radical, for example those in which X represents an $NOCH_3$ radical, there can also be mentioned as preferred compounds, the compounds of formula (I) in which $R_1$ represents an alkyl radical optionally interrupted by an oxygen or sulphur atom, an O-alkyl radical, optionally interrupted by an oxygen or sulphur atom, an $NH_2$ radical, for example the compounds in which $R_1$ is a $CH_3$,

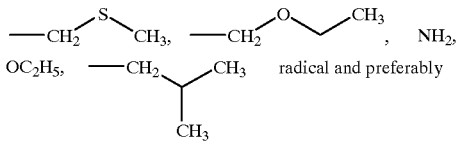

the compounds of formula (I) in which $R_1$ represents a methyl or O-ethyl radical.

Among the preferred compounds of the invention, there can be quite especially mentioned the compounds whose preparation is given hereafter in the experimental part and in particular the following compounds:

5-methyl-1H-pyrrole-2-carboxylic acid 3'-ester of 3-acetyl-7-((6-deoxy-5-C-methyl-4-O-methyl-alpha-L-lyxo-hexop yranosyl)oxy)-4-hydroxy-8-methyl-2H-1-benzopyran-2-one, 5-methyl-1H-pyrrole-2-carboxylic acid 3'-ester of ethyl 7((6-deoxy-5-C-methyl-4-O-methyl-alpha-L-lyxo-hexopyranosyl)oxy)-4-hydroxy-8-methyl-2-oxo-2H-1-benzopyran-3-carboxylate, 5-methyl-1H-pyrrole-2-carboxylic acid 3'-ester of 7-((6-deoxy-5-C-methyl-4-O-methyl-alpha-L-lyxo-hexopyranosyl)oxy)-4-hydroxy-3-(1-(methoxyimino)-ethyl)-8-methyl-2H-1-benzopyran-2-one, 5-methyl-1H-pyrrole-2-carboxylic acid 3'-ester of 7-((6-deoxy-5-C-methyl-4-O-methyl-alpha-L-lyxo-hexopyranosyl)oxy)-3-(ethoxyacetyl)-4-hydroxy-8-methyl-2H-1-benzopyran-2-one, 5-methyl-1H-pyrrole-2-carboxylic acid 3'-ester of 3-(cyclopropylcarbonyl)-7-((6-deoxy-5-C-methyl-4-O-methyl-alp ha-L-lyxo-hexopyranosyl)-oxy)-4-hydroxy-8-methyl-2H-1-benzopyran-2-one, 5-methyl-1H-pyrrole-2-carboxylic acid 3'-ester of 7-((6-deoxy-5-C-methyl-4-O-methyl-alpha-L-lyxo-hexopyranosyl)oxy)-4-hydroxy-8-methyl-2-oxo-2H-1-benzopyran-3-carboxamide, The products of general formula (I) have a very good antibiotic activity on gram + bacteria such as staphylococci, streptococci, pneumococci, enterococci, listeria, anaerobes.

The compounds of the invention can therefore be used as medicaments in the treatment of infections caused by susceptible germs and in particular, in that of staphylococcia, such as staphylococcal septicemias, malignant staphylococcia of the face or skin, pyodermatitis, septic or suppurating wounds, boils, anthrax, phlegmons, erysipelas and acne, staphylococcia such as acute primary or post-influenzal angina, bronchopneumonia, pulmonary suppuration, streptococcia such as acute anginas, otitis, sinusitis, scarlet fever, pneumococcia such as pneumonia, bronchitis and diphteria. The products of the present invention are also active against infections caused by germs such as Haemophilus influenzae.

Therefore a subject of the invention is the compounds of formula (I) as medicaments.

A more particular subject of the invention is, as medicaments, the compounds indicated above as preferred compounds.

A subject of the invention is also the pharmaceutical compositions containing at least one of the medicaments defined above as active ingredient.

These compositions can be administered by buccal, rectal, parenteral route or by local route as a topical application on the skin and mucous membranes, but the preferred administration route is the buccal route. They can be solid or liquid and be presented in the pharmaceutical forms currently used in human medicine, such as for example, plain or sugar-coated tablets, capsules, granules, suppositories, injectable preparations, ointments, creams, gels; they are prepared according to the usual methods. The active ingredient or ingredients can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

These compositions can also be presented in the form a powder intended to be dissolved extemporaneously in an appropriate vehicle, for example apyrogenic sterile water.

The dose administered is variable according to the illness treated, the patient in question, the administration route and the product considered. It can be, for example, comprised between 50 mg and 3000 mg per day by oral or injectable route, in an adult for the preferred products.

A subject of the invention is also a process characterized in that a compound of formula (II):

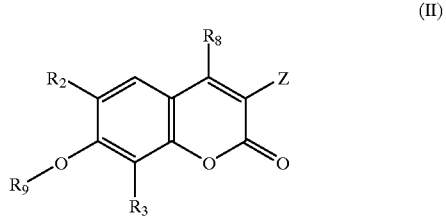

(II)

in which $R_8$ represents a free or blocked hydroxyl radical, Z represents hydrogen or a

radical, X, $R_1$, $R_2$ and $R_3$ retain their previous meaning, $OR_9$ represents a free or blocked hydroxyl radical, is subjected to the action of a compound of formula (III):

(III)
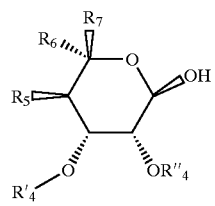

in which $R_5$, $R_6$ and $R_7$ retain their previous meaning, $OR'_4$ represents a blocked hydroxyl radical, $R''_4$ represents a hydrogen atom or $R'_4$ and $R''_4$ form together with the carbon atoms to which they are joined a cycle

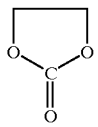

in order to obtain the compound of formula (IV):

(IV)
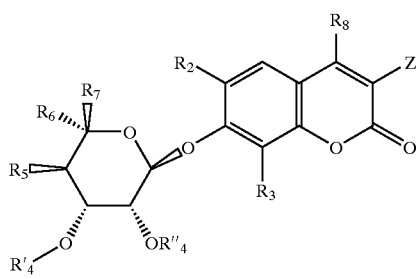

in which the substituents retain their previous meaning, then the compound of formula (IV) thus obtained is subjected to the following steps, in total or in part
  release of the hydroxyl in position 4 after optional blocking of the hydroxyl of the sugar in alpha position of $OR'_4$,
  if Z represents a hydrogen atom introduction of the

radical after optional blocking of the hydroxyls which are able to react,
  introduction of the

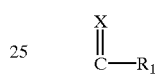

radical by substitution of this radical by the $R'_4$ radical, modification of the X radical.

The starting products of the invention, namely, the products of formulae (II) and (III) are new products, examples of the preparation of these compounds are given hereafter in the experimental part.

The compounds of formula (IV) obtained during the implementation of the process of the invention are new.

Therefore a subject of the invention is, as new chemical products, the compounds of formulae (II), (III) and (IV).

In a preferred implementation of the process of the invention:
  the reaction between the compounds of formulae (II) and (III) takes place in the presence of a dialkyl azodicarboxylate such as diethyl or diisopropyl azodicarboxylate,
  the optional release of the hydroxyl in position 4 of the coumarin, is carried out by hydrogenolysis or by isomerization then hydrolysis,
  the other protected hydroxyls are released by acid hydrolysis for example, in the presence of paratoluene sulphonic acid,
  the introduction of the

radical when Z represents hydrogen, is carried out by acylation then transposition,
  the glycosylation takes place by Mitsunobu's reaction.
  the other modifications are carried out under standard conditions.

The following examples illustrate the invention without however limiting it.

PREPARATION 1

3-(5-methyl-1H-pyrrole-2-carboxylate) of 6-deoxy-5-C-methyl-4-O-methyl-L-lyxohexopyranose Stage A: phenylmethyl 6-deoxy-5-C-methyl-4-O-methyl-L-lyxo-hexopyranoside A stream of hydrochloric acid gas is bubbled through a suspension containing 80 g of 6-deoxy 5-C-methyl-4-O-methyl-L-lyxohexopyranose and 400 ml of benzyl alcohol for 2 hours at 20~22° C. 120 ml of demineralized water is added and 40 g of sodium carbonate is added, then 240 ml of ethyl acetate. After decanting and extracting with ethyl acetate, the organic phases are combined and washed with a saturated solution of sodium chloride. Followed by drying, separating, rinsing and distilling under agitation and under vacuum at 45~50 mb. The benzyl alcohol is distilled under vacuum at 2 mb. 118.8 g of a product is obtained which is purified by chromatography on silica eluting with a methylene chloride/methanol mixture (95-5). In this way 109.9 g of sought product is obtained.

Stage B: phenylmethyl-2,3-O-carbonyl-6-deoxy-5-C-methyl-4-O-methyl-L-lyxo-hexopyranoside 67.5 g of 1,1-carbonyldiimidazole is added to a solution containing 109 g of the product prepared in Stage A and 1.1 l of dichloro-1-2-ethane. The reaction medium is taken to reflux for 2 hours. The temperature is returned to 20~22° C. then the reaction medium is brought to dryness under reduced pressure at 25~30° C. 200.8 g of product is obtained which is purified by chromatography on silica eluting with a methylene chloride-methanol mixture (99-1). 91.6 g of sought product is obtained.

| I.R. Spectrum: | |
| --- | --- |
| Ketone | 1813 cm$^{-1}$ |
| benzyl | 1498 cm$^{-1}$ |

The 2-1H-pyrrole used in Stage C was prepared as follows:

750 g of pure caustic potash is added to a suspension containing 5 l of ethylene glycol and 370 g of 2-carboxaldehyde pyrrole. Then 544 cm$^3$ of 64% hydrazine hydrate is added over 30 minutes. The reaction medium is taken to reflux for 1 hour 30 minutes and 2 l of demineralized water is added then it is poured into a water-ice mixture. Extraction is carried out with methylene chloride, followed by drying, separating, rinsing and bringing to dryness. 270.3 g of product is obtained which is purified by distillation under pressure of 15 millibars. 227 g of sought product is collected.

Tbp=46~47° C. under 15 millibars.

Stage C: 3-(5-methyl-1H-pyrrole-2-carboxylate) of phenyl-methyl-6-deoxy-5-C-methyl-4-O-methyl-L-lyxo-hexopyranoside A solution containing 60.2 g of 2-methyl-1H-pyrrole in 460 ml of ethyl ether is added over one hour at 0~2° C. to 248 ml of a 3M solution of methylmagnesium bromide in ether. The reaction medium is maintained under agitation at 0~2° C. for 30 minutes and 460 cm$^3$ of toluene dethiophene is added over 15 minutes. Agitation is carried out for 15 minutes at 0±2° C. and a solution of 91.3 g of the product prepared in Stage B and 460 ml of toluene dethiophene are introduced over 45 minutes. Agitation is maintained for 2 hours at 0±2° C. The reaction medium is poured into an aqueous solution of ammonium chloride, followed by decanting, extracting with ethyl acetate, washing, drying, rinsing and bringing to dryness under reduced pressure. 134.6 g of product is obtained which is purified by chromatography on silica eluting with a methylene chloride-acetone mixture (8-2), then (9-1). In this way the sought product is obtained.

Stage D: 3-(5-methyl-1H-pyrrole-2-carboxylate) of 6-deoxy-5-C-methyl-4-O-methyl-L-lyxohexopyranose 14.7 of 10% palladium on activated carbon is added to a solution containing 72.4 g of the product prepared in Stage C and 1.45 l of denatured ethanol 100. The reaction medium is maintained under hydrogen pressure for 1 hour at 60~62° C. The reaction medium is allowed to return to ambient temperature. Another 1.5 g of 10% palladium on activated carbon is added. Agitation is carried out under hydrogen pressure for 1 hour. The temperature is returned to 20~22° C., followed by separating, filtering, rinsing, and after bringing to dryness, 57 g of sought product is obtained.

PREPARATION 2

7-hydroxy-8-methyl-4-(2-propenyloxy)-2H-1-benzopyran-2-one

Stage A: 1-[2-hydroxy-3-methyl-4-[(tetrahydro-2H-pyran-2-yl)oxy]phenyl ethanone

A mixture containing 200 g of 1-[2,4-dihydroxy-3-methyl]phenyl ethanone and 1.2 l of ethyl ether is cooled down to 8° C. 200 ml of dihydro-2H-pyran and 1 g of PTSA are added. The reaction medium is left to return to ambient temperature. Agitation is carried out for 3 hours and 253 mg of PTSA is added. The product obtained is poured into 400 ml of a molar aqueous solution of potassium acid phosphate, followed by decanting, washing with water and drying. After evaporation 302.5 g of crude sought product is obtained which is purified thus: the product is diluted in 2 l of methylene chloride, the organic phase is washed with ammonium hydroxide diluted to one tenth, then with brine, dried, filtered and evaporated to dryness. 272.55 g of sought product is obtained.

Stage B: 4-hydroxy-8-methyl-7-[(tetrahydro-2H-pyran-2-yl)oxy]-2H-1-benzopyran-2-one A mixture containing 750 ml of toluene, 129.9 g of the product prepared in Stage A and 126 ml of diethyl carbonate in 620 ml of toluene is heated to 90° C. 52 g of sodium hydride at 55% in oil is added while maintaining the temperature at 90° C. The reaction medium is maintained under agitation at 90° C. and left to return to ambient temperature. 10 ml of ethyl alcohol is added, followed by separating and rinsing with ethyl ether, then separating. The whole is poured into 1 l of a molar aqueous solution of sodium acid phosphate, followed by separating and rinsing with water, with acetone and with ether. A product is obtained which is dried at 50° C. in the presence of $P_2O_5$. 141.89 g of sought product is obtained.

Stage C: 8-methyl-4-(2-propenyloxy)-7-[(tetrahydro-2H-pyran-2-yl)oxy]-2H-1-benzopyran-2-one 9.45 ml of diethyl azocarboxylate is added at 0° C. to a mixture containing 13.814 g of the product prepared in the preceding stage, 4.07 ml of allyl alcohol, 15.74 g of triphenylphosphine and 150 ml of dichloromethane. The reaction medium is maintained under agitation for 15 minutes at 0° C. then for 2 hours at ambient temperature. Another 5.25 g of triphenylphosphine, 1.36 ml of allyl alcohol and 3.15 ml of diethyl azodicarboxylate are added. The reaction medium is agitated for 2 hours at ambient temperature. After concentration, the product obtained is chromatographed on silica eluting with a hexane-ethyl acetate mixture (3-1).

7.85 g of product is obtained.

Stage D: 7-hydroxy-8-methyl-4-(2-propenyloxy)-2H-1-benzopyran-2-one

A mixture containing 7.80 g of the product prepared in the preceding stage in 150 ml of tetrahydrofuran to which 100 ml of a 1M solution HCl has been added is agitated for 6 hours at ambient temperature. Then a saturated solution of sodium chloride is added and extraction is carried out with ethyl acetate. The organic phase is dried over magnesium sulphate and concentrated to dryness. After drying 4.40 g of sought product is obtained.

rf=0.26 hexane ethyl acetate (1-1).

EXAMPLE 1

5-methyl-1H-pyrrole-2-carboxylic acid-3'-ester of 7-((6-deoxy-5-C-methyl-4-O-methyl-alpha-L-lyxo-hexopyranosyl)oxy)-4-hydroxy-8-methyl-3-((methylthio)acetyl)-2H-1-benzopyran-2-one Stage A: 5-methyl-1H-pyrrole-2-carboxylic acid 3'-ester of 7-[(6-deoxy-5-C-methyl-4-O-methyl-alpha-L-lyxo-hexopyranosyl)oxy]-8-methyl-4-(2-propenyloxy)-2H-1-benzopyran-2-one 5 g of the product of Preparation 1, 4.65 g of the product of Preparation 2 and 5.26 g of triphenylphosphine and 500 ml of dichloromethane are mixed together. Then 4 ml of diisopropylazodicarboxylate is added at 0° C. Agitation is carried out for 1 hour at ambient temperature. 2.19 g of triphenylphosphine and 1.65 ml of diethyl azodicarboxylate are added. Agitation is carried out for 1 hour at ambient temperature and another 2.19 g of triphenylphosphine and 1.65 ml of diisopropylazodicarboxylate are added. Washing is carried out with an aqueous solution of sodium dihydrogen phosphate, and with brine, followed by drying, filtering and concentrating to dryness. After chromatography on silica eluting with a hexane-ethyl acetate mixture (60-40), on the one hand, 3.51 g of product A is obtained which is triturated in ethyl ether, followed by separating and drying. 3.0 g of crude sought product is obtained.

On the other hand, 3.24 g of product B is obtained, which is chromatographed on silica eluting with a methylene chloride, ethyl acetate mixture, 90-10 then 80-20, then with a methylene chloride, ethyl acetate, tetrahydrofuran mixture (70-20-10), and 0.88 g of product is obtained which is triturated under ultrasound in ethyl ether. After separation the crude sought product is obtained.

The two quantities of crude sought product are combined, triturated in the ethyl ether, separated and dried. 3.625 g of sought product is obtained.

Stage B: 5-methyl-1H-pyrrole-2-carboxylic acid-3'-ester of 7-[(6-deoxy-5-C-methyl-4-O-methyl-2-O-(tetrahydro-2H-pyran-2-yl)-alpha-L-lyxo-hexopyranosyl)oxy]-8-methyl-4-(2-propenyloxy)-2H-1-benzopyran-2-one 200 mg of paratoluenesulphonic acid (PTSA) and 11 g of the product obtained in the preceding stage are added to 3.77 ml of dihydro-(2H)-pyran. The reaction medium is agitated at ambient temperature for 2 hours. The reaction medium is treated with a saturated solution of sodium hydrogen carbonate. Extraction is carried out with methylene chloride. The organic phases are combined and dried. The solvent is evaporated to dryness and the residue is triturated in a hexane-ethyl acetate mixture (3-1). After separating and drying 8.40 g of sought product is obtained.

Stage C: 5-methyl-1H-pyrrole-2-carboxylic acid-3'-ester of 7-[(6-deoxy-5-C-methyl-4-O-methyl-2-O-(tetrahydro-2H-pyran-2-yl)-alpha-L-lyxo-hexopyranosyl)-oxy]-4-hydroxy-8-methyl-2H-1-benzopyran-2-one 5.88 ml of isopropylamine and 1.67 g of palladium tetrakistriphenylphosphine is added at 0° C. to a solution of 8.90 g of the product prepared in the preceding stage and 90 ml of tetrahydrofuran. The reaction mixture is agitated at 0° C. for 20 minutes and it is poured into a mixture of 50 ml of an aqueous solution of sodium hydrogen sulphate and 100 ml of a hexane-ethyl acetate mixture 1-2. The aqueous phase is extracted with a hexane-ethyl acetate mixture (1-2). The organic phases are combined and dried. The solvents are evaporated off and the residue is purified by chromatography on silica eluting with a methylene chloride-methanol mixture (95-5). 2.50 g of sought product is obtained.

rf=0.22 $CH_2Cl_2$—$CH_3OH$ (95-5).

Stage D: 5-methyl-1H-pyrrole-2-carboxylic acid-3'-ester of 7-[(6-deoxy-5-C-methyl-4-O-methyl-2-O-(tetrahydro-2H-pyran-2-yl)-alpha-L-lyxo-hexopyranosyl)-oxy]-4-hydroxy-8-methyl-3-[(methylthio)acetyl]-2H-1-benzopyran-2-one A solution is prepared containing 400 mg of the product prepared in the preceding stage and 5 ml of anhydrous dichloromethane. 67 µl of 2-methylthioacetic acid, 280 mg of 4-dimethylaminopyridine and 147 mg of N-(3-dimethylamino-propyl)-N'-ethylcarbodiimide hydrochloride are added. The reaction medium is maintained under agitation for 18 hours at ambient temperature. Dilution is carried out with 100 ml of ethyl acetate, followed by washing with an aqueous solution of sodium hydrogen sulphate, with water and with brine, drying, filtering and concentrating to dryness. 401 mg of product is obtained which is purified by chromatography eluting with a chloroform methanol mixture (98-2). After drying 324 mg of sought product is obtained.

rf=0.68 eluant=methylene chloride-methanol (95-5).

Stage E: 5-methyl-1H-pyrrole-2-carboxylic acid-3'-ester of 7-[(6-deoxy-5-C-methyl-4-O-methyl-alpha-L-lyxo-hexopyranosyl)oxy]-4-hydroxy-8-methyl-3-[(methylthio)-acetyl]-2H-1-benzopyran-2-one 60 mg of paratoluenesulphonic acid (PTSA) is added to a solution containing 293 mg of the product prepared in the preceding stage and 10 ml of methanol. The reaction medium is agitated for 5 hours at ambient temperature. The reaction medium is diluted with an ethyl acetate-hexane mixture (67-33) and washed with a dilute solution of sodium bicarbonate, followed by rinsing with water then with brine. After drying and evaporating to dryness, 227 mg of product is obtained which is chromatographed on silica eluting with a chloroform-methanol mixture (93-7). 171 mg of crude sought product is collected which is chromatographed on silica eluting with a chloroform-methanol mixture (94-6). In this way the sought product is isolated.

rf=0.42 $CHCl_3$—$CH_3OH$ (94-6).

NMR of the proton (300 MHz, DMSO-$d_6$, ppm) 1.06 (s, 3H), 1.31 (s, 3H), 2.11 (s, 3H), 2.23 (s, 3H), 2.25 (s, 3H), 3.47 (s, 3H), 3.66 (d, 1H, J=10 Hz), 3.92 (AB, 2H, J=14.0 Hz), 4.19 (s, 1H), 5.48 (dd, 1H, J=3.0 and 10.0 Hz), 5.70 (d, 1H, J=2.5 Hz), 5.74 (m, 1H), 5.93 (m, 1H), 6.79 (m, 1H), 7.26 (d, 1H, J=9.0 Hz), 7.94 (d, 1H, J=9.0 Hz), 11.66 (ws, 1H).

EXAMPLE 2

5-methyl-1H-pyrrole-2-carboxylic acid-3'-ester of 7-((6-deoxy-5-C-methyl-4-O-methyl-alpha-L-lyxo-hexopyranosyl)oxy)-3-(ethoxyacetyl)-4-hydroxy-8-methyl-2H-1-benzopyran-2-one Stage A: 5-methyl-1H-pyrrole-2-carboxylic acid-3'-ester of 7-[(6-deoxy-5-C-methyl-4-O-methyl-2-O-(tetrahydro-2H-pyran-2-yl)-alpha-L-lyxo-hexopyranosyl)-oxy]-3-(ethoxyacetyl)-4-hydroxy-8-methyl-2H-1-benzopyran-2-one 55 µl of 2-ethoxyacetic acid is added to solution containing 300 mg of the product prepared in Stage C of the preceding example, 210 mg of 4-dimethylaminopyridine (DMAP) and 110 mg of N-(3-dimethylaminopropyl-N'-ethylcarbodiimide. Agitation is carried out for 18 hours at ambient temperature. The reaction medium is diluted with 100 ml of ethyl acetate, washed with a lot aqueous solution of sodium hydrogen sulphate, with water then with brine. The organic phase is dried, filtered and concentrated. 362 mg of product is obtained which is purified by chromatography on silica eluting with a methylene chloride-methanol mixture 97.5-2.5. The solvents are evaporated off and the product obtained is dried under reduced pressure. In this way 265 mg of sought product is obtained. rf=0.30, eluant methylene chloride-methanol (95-5).

Stage B: 5-methyl-1H-pyrrole-2-carboxylic acid-3'-ester of 7-((6-deoxy-5-C-methyl-4-O-methyl-alpha-L-lyxo-hexopyranosyl)oxy)-3-(ethoxyacetyl)-4-hydroxy-8-methyl-2H-1-benzopyran-2-one 50 mg of p-toluenesulphonic acid is added to a solution containing 245 mg of the product obtained in Stage A and 10 ml of methanol. Agitation is carried out for 5 hours at ambient temperature, followed by dilution with an ethyl acetate-hexane mixture, washing with a dilute solution of sodium bicarbonate, rinsing with water, with brine, drying and evaporating to dryness. 163 mg of product is obtained which is chromatographed on silica eluting with a methylene chloride-methanol mixture (92-8). 116 mg of product is obtained. rf=0,20 chloroform-methanol (94-6).

NMR of the proton (300 MHz, DMSO-$d_6$, ppm) 1.07 (s, 3H), 1.17 (t, 3H, J=7.0 Hz), 1.30 (s, 3H), 2.22 (s, 3H), 2.26 (s, 3H), 3.56 (q, 2H, J=7.0 Hz), 3.66 (d, 1H, J=10.0 Hz), 4.18 (m, 1H), 4.71 (ws, 2H), 5.48 (dd, 1H, J=3.0 and 10.0 Hz), 5.66 (ws, 1H), 5.72 (d, 1H, J=5.0 Hz), 5.93 (m, 1H), 6.78 (m, 1H), 7.21 (d, 1H) J=9.0 Hz), 7.90 (d d, 1H, J=9.0 Hz), 11.65 (ws, 1H), 15.25 (very wide, 1H).

EXAMPLE 3

(Z) 5-methyl-1H-pyrrole-2-carboxylic acid-3'-ester of 7-((6-deoxy-5-C-methyl-4-O-methyl-alpha-L-lyxo-hexopyranosyl)oxy)-4-hydroxy-3-(1-hydroxy-2-(2-pyridinyl)ethenyl)-8-methyl-2H-1-benzopyran-2-one Stage A: (Z) 5-methyl-1H-pyrrole-2-carboxylic acid-3'-ester of 7-[(6-deoxy-5-C-methyl-4-O-methyl-2-O-(tetrahydro-2H-pyran-2-yl)-alpha-L-lyxo-hexopyranosyl)-oxy]-4-hydroxy-3-(1-hydroxy-2-(2-pyridinyl)-ethenyl)-8-methyl-2H-1-benzopyran-2-one The operation is carried out as in Stage A of the preceding example starting from 300 mg of the product of Stage C of Example 1 and 100 mg of the hydrochloride of 2-pyridylacetic acid, 135 mg of sought product is obtained.

rf=0.64 $CH_2Cl_2$/THF (50-50)

rf=0.45 $CH_2Cl_2$/MeOH (94-6).

Stage B: (Z) 5-methyl-1H-pyrrole-2-carboxylic acid-3'-ester of 7-((6-deoxy-5-C-methyl-4-O-methyl-alpha-L-lyxo-hexopyranosyl)-oxy)-4-hydroxy-3-(1-hydroxy-2-(2-pyridinyl)ethenyl)-8-methyl-2H-1-benzopyran-2-one The operation is carried out as in the last stage of Example 1 and 29 mg of sought product is obtained, starting from 135 mg of the product prepared in Stage A.

NMR of the proton (300 MHz, DMSO-$d_6$, ppm) 1.09 (s, 3H), 1.30 (s, 3H), 2.23 (s, 3H), 2.25 (s, 3H), 3.48 (s, 3H), 3.66 (d, 1H, J=10.0 Hz), 4. 16 (m, 1H), 5.49 (dd, 1H, J=3.0 and 10.0 Hz), 5.60 (d, 1H, J=2.0 Hz), 5.93 (m, 1H), 6.78 (m, 1H), 6.82 (s, 1H), 7.08 (dd, 1H, J=5.0 and 7.5 Hz), 7.12 (d, 1H, J=9.0 Hz), 7.62 (d, 1H, J=8.0 Hz), 7.80 (d, 1H, J=9.0 Hz), 7.94 (dd, 1H, J=7.5 and 8 Hz), 8.16 (d, 1H, J=5 Hz), 11.65 (ws, 1H), 13.04 (m, 1H), 13.81 (m, 1H).

PREPARATION 3 ethyl 7-hydroxy 8-methyl-2-oxo-4-(phenyl-methoxy)-2H-1-benzopyran-3-carboxylate

Stage A: ethyl 4-hydroxy-8-methyl-2-oxo-7-[(tetrahydro-2H-pyran-2-yl)oxy]-2H-1-benzopyran-3-carboxylate 106.7 g of DMAP is added to a mixture of 1.2 l of methylene chloride and 120.65 g of the product prepared in Stage B of Preparation 2. The mixture obtained is cooled down with an ice bath and 57.1 ml of ethyl chloroformate is introduced over 50 minutes while keeping the temperature below 5° C. Another 26.6 g of DMAP and 21 ml of ethyl chloroformate are added, then another 21.3 g of DMAP and 8.4 ml of ethyl chloroformate are added. The reaction medium is poured into 1 l of a molar aqueous solution of sodium acid phosphate 1M ($NaHPO_4$) then sodium acid phosphate in powder form in order to obtain a pH equal to 6. The aqueous phase is extracted with methylene chloride. The organic phases are combined and washed with a 1N solution of HCl, followed by washing with water, decanting, drying, filtering and bringing to dryness.

144.63 g of sought product is obtained.

Stage B: ethyl-8-methyl-2-oxo-4-(phenylmethoxy)-7-[(tetrahydro-2H-pyran-2-yl)oxy]-2H-1-benzopyran-3-carboxylate 76 ml of dialkyl azodicarboxylate (DEAD) is introduced over 1 hour 30 minutes at 0° C. into a solution containing 1.2 l of methylene chloride, 120.90 of the product prepared in the preceding stage, 54 ml of benzyl alcohol and 109.1 g of triphenylphosphine. Filtration is carried out and the filtrate is poured into 500 ml of a 1M solution of sodium acid phosphate. Extraction is carried out with methylene chloride followed by washing, drying, filtering and bringing to dryness. 355.5 g of product is obtained which is taken up in methylene chloride. The reaction mixture is left overnight in a refrigerator. After filtering the filtrate is evaporated and dried. 324.7 g of product is obtained which is taken up in isopropyl ether, agitated, filtered, rinsed with ether and dried. Evaporation is carried out under reduced pressure and 251 g of crude product is obtained which is purified by chromatography on silica, eluting with methylene chloride then with a methylene chloride-ethyl acetate mixture (90-10). In this way the sought product is obtained.

Stage C: ethyl 7-hydroxy 8-methyl-2-oxo-4-(phenylmethoxy)-2H-1-benzopyran-3-carboxylate 1 l of a 1N solution of HCL is introduced into a solution containing 90 g of the product prepared in the preceding stage and 2 l of THF. Agitation is carried out for 4 hours at ambient temperature. 2 l of methylene chloride is added followed by washing with a 10% aqueous solution of sodium bicarbonate, then with salt water. After drying and evaporating to dryness, the product is impasted in ether, separated, rinsed and dried under reduced pressure. 59.8 g of sought product is obtained.

rf=0.15 $CH_2Cl_2$—$CH_3CO_2Et$ (95-5).

NMR Spectrum DMSO

| | |
|---|---|
| H in position 6 | 6.89 ppm |
| H of OH | 10.71 (s) ppm |
| H of the methoxy | 5.29 (s) ppm |
| H of $\underline{CH_2}CH_3$ | 4.33 (a) |
| H of $CH_2\underline{CH_3}$ | 1.29 (t) |
| H of the methyl in position 8 | 2.16 (s) ppm |

EXAMPLE 4

5-methyl-1H-pyrrole-2-carboxylic acid-3'-ester of ethyl 7-((6-deoxy-5-C-methyl-4-O-methyl-alpha-L-lyxo-hexopyranosyl)-oxy)-4-hydroxy-8-methyl-2-oxo-2H-1-benzopyran-3-carboxylate Stage A: 5-methyl-1H-pyrrole-2-carboxylic acid-3'-ester of ethyl-7-[(6-deoxy-5-C-methyl-4-O-methyl-alpha-L-lyxo-hexopyranosyl)-oxy]-8-methyl-2-oxo-4-(phenylmethoxy)-2H-1-benzopyran-3-carboxylate The operation is carried out as in Example 1 Stage A, starting from the products of Preparations 1 and 3, the sought product is obtained. rf=0.55 ethyl ether-hexane 1-2

Stage B: 5-methyl-1H-pyrrole-2-carboxylic acid-3'-ester of ethyl-7-((6-deoxy-5-C-methyl-4-O-methyl-alpha-L-lyxo-hexopyranosyl)-oxy)-4-hydroxy-8-methyl-2-oxo-2H-1-benzopyran-3-carboxylate 35 mg of 10% palladium on carbon is added to a solution containing 330 mg of the product prepared in Stage A and 10 ml of absolute ethanol. The mixture is agitated for 5 hours at ambient temperature under a slight hydrogen pressure. After filtering, the ethanol is evaporated to dryness, the residue is triturated under ultrasound in the presence of isopropyl ether. After separating and drying, 189.4 mg of sought product is obtained.

rf=0.43 $CH_2Cl_2$—MeOH (91-9).

NMR of the proton (300 MHz, DMSO-$d_6$, ppm) 1.07 (s, 3H), 1.30 (s, 3H), 1.32 (t, 3H, J=7.0 Hz), 2.22 (s, 3H), 2.25 (s, 3H), 3.48 (s, 3H), 3.66 (d, 1H, J=10.0 Hz), 4.18 (ws, 1H), 4.37 (q, 2H, J=7.0 Hz), 5.48 (dd, 1H, J=3.0 and 10.0 Hz), 5.66 (d, 1H, J=2.0 Hz), 5.73 (ws, 1H), 5.93 (t, 1H, J=3 Hz), 6.78 (t, 1H, J=3.0 Hz), 7.23 (d, 1H H, J=9.0 Hz), 7.86 (d, 1H, J=9.0 Hz), 11.66 (ws, 1H).

EXAMPLE 5

5-methyl-1H-pyrrole-2-carboxylic acid-3'-ester of 3-acetyl-7-((6-deoxy-5-C-methyl-4-O-methyl-alpha-L-lyxo-hexopyranosyl)oxy)-4-hydroxy-8-methyl-2H-1-benzopyran-2-one Stage A: ethyl 7-((6-deoxy-5-C-methyl-4-O-methyl-alpha-L-lyxo-hexopyranosyl)-oxy)-8-methyl-2-oxo-4-(phenylmethoxy)-2H-1-benzopyran-3-carboxylate 136 µl of acetic acid is added to a solution containing 1 g of the product prepared in Stage C of Example 1, 746 mg of 4-dimethylaminopyridine, 433 mg of N-(3-dimethyl aminopropyl)-N'-ethylcarbodiimide hydrochloride and 20 ml of dichloromethane. The reaction mixture is agitated for 16 hours at ambient temperature and diluted with dichloromethane. The resulting solution is washed with a 10% aqueous solution of sodium hydrogen sulphate, followed by drying, filtering and concentrating to dryness. The reaction mixture is triturated in a hexane-ethyl acetate mixture (2-1). After separating and drying, 634 mg of sought product is obtained. rf=0.63 $CH_2Cl_3$—MeOH (94-6).

Stage B: 5-methyl-1H-pyrrole-2-carboxylic acid-3'-ester of 3-acetyl-7-((6-deoxy-5-C-methyl-4-O-methyl-alpha-L-lyxo-hexopyranosyl)oxy)-4-hydroxy-8-methyl-2H-1-benzopyran-2-one 80 mg of paratoluenesulphonic acid is added to a solution containing 568.4 mg of the product prepared in Stage A, 20 ml of methanol and 15 ml of dichloromethane. Agitation is carried out at ambient temperature for 4 hours. The reaction mixture is poured into a mixture of dichloromethane and a saturated aqueous solution of sodium bicarbonate. The aqueous phase is extracted with dichloromethane, followed by drying, filtering and concentrating to dryness under reduced pressure. 254 mg of sought product is obtained. rf=0.39 $CH_2Cl_3$—MeOH (94-6).

NMR of the proton (300 MHz, DMSO-$d_6$, ppm) 1.06 (s, 3H), 1.30 (s, 3H), 2.22 (s, 3H), 2.24 (s, 3H), 2.66 (s, 3H), 3.47 (s, 3H), 3.66 (d, 1H, J=9.5 Hz), 4.18 (ws, 1H), 5.48 (dd, 1H, J=3 and 9.5 Hz), 5.69 (d, 1H, J=2.5 Hz), 5.75 (d, 1H, J=5 Hz), 5.93 (t, 1H, J=3.0 Hz), 6.79 (t, 1H, J=3.0 Hz), 7.25 (d, 1H, J=8.5 Hz), 7.92 (d, 1H H, J=8 Hz), 11.66 (ws, 1H), 15.44 (ws, 1H).

PREPARATION 4

2-methylpropyl 7-hydroxy 8-methyl-2-oxo-4-(phenylmethoxy)-2H-1-benzopyran-3-carboxylate Stage A: [8-methyl-2-oxo-7-[(tetrahydro-2H-pyran-2-yl)oxy]-2H-1-benzopyran-4-yl]2-methylpropyl carbonate 6.96 ml of triethylamine then 3.57 ml of isobutyl chloroformate are added to a solution containing 6.907 g of the product of Preparation 2 Stage B and 40 ml of tetrahydrofuran. Agitation is carried out for 1 hour at ambient temperature, followed by diluting with tetrahydrofuran, washing with a 10% aqueous solution of sodium hydrogen sulphate, drying and concentrating to dryness. After triturating under ultrasound in the presence of a hexane-ethyl acetate mixture (2-1), separation and drying are carried out. 7.475 g of product is obtained.

rf=0.74 $CH_2Cl_2$—MeOH (94-6).

Stage B: 2-methylpropyl 4-hydroxy-8-methyl-2-oxo-7-[(tetra-hydro-2H-pyran-2-yl)-oxy]-2H-1-benzopyran-3-carboxylate 2.37 g of DMAP is added to a solution containing 7.30 g of the product prepared in Stage A in 50 ml of dichloromethane. Agitation is carried out for 5 hours at ambient temperature. The reaction mixture is diluted with methylene chloride, washed with a 10% aqueous solution of sodium hydrogen sulphate, dried and concentrated under pressure reduced. The product obtained is chromatographed on silica eluting with a hexane-ethyl acetate mixture (1-1). The solvents are evaporated off followed by drying. 3.0 g of sought product is obtained.

rf=0.38 hexane-ethyl acetate (1-1).

Stage C: 2-methylpropyl-8-methyl-2-oxo-4-(phenylmethoxy)-7-[(tetrahydro-2H-pyran-2-yl)-oxy]-2H-1-benzopyran-3-carboxylate 1.422 ml of diethyl azodicarboxylate is added at 0° C. to a mixture containing 2.80 g of the product prepared in the preceding stage, 928 ul of benzyl alcohol and 2.34 g of triphenylphosphine. Agitation is carried out for 2 hours at ambient temperature. 976 mg of triphenylphosphine and 585 ul of diethyl azodicarboxylate are added and agitation is carried out for 2 hours at ambient temperature. After concentrating, chromatography is carried out on silica eluting with a hexane-ethyl acetate mixture (2-1). The solvents are evaporated off followed by drying. 2.18 g of sought product is obtained.

rf=0.25 hexane-ethyl acetate (2-1).

Stage D: 2-methylpropyl 7-hydroxy 8-methyl-2-oxo-4-(phenyl-methoxy)-2H-1-benzopyran-3-carboxylate 35 ml of a 1M aqueous solution of hydrochloric acid is added to a solution containing 2.00 g of the product prepared in the preceding stage and 70 ml of tetrahydrofuran. Agitation is carried out for 7 hours at ambient temperature, followed by diluting with a hexane-ethyl acetate mixture (1-1). The phases are separated and the aqueous phase is extracted with a hexane-ethyl acetate mixture (1-1). The organic phases are combined and washed with a 1M solution of sodium dihydrogen phosphate, dried and concentrated to dryness. The residue is triturated under ultrasound in a hexane-ethyl acetate mixture (4-1). After separating and drying 1.27 g of product is collected.

rf=0.64 methylene chloride-methanol (94-6).

EXAMPLE 6

5-methyl-1H-pyrrole-2-carboxylic acid-3'-ester of 2-methylpropyl-7-[(6-deoxy-5-C-methyl-4-O-methyl-alpha-L-lyxo-hexopyranosyl)-oxy]-4-hydroxy-8-methyl-2-oxo-2H-1-benzopyran-3-carboxylate Stage A: 5-methyl-1H-pyrrole-2-carboxylic acid-3'-ester of 2-methylpropyl-7-[(6-deoxy-5-C-methyl-4-O-methyl-alpha-L-lyxo-hexopyranosyl)-oxy]-8-methyl-2-oxo-4-(phenylmethoxy)-2H-1-benzopyran-3-carboxylate The operation is carried out as in Example 1 Stage A, starting from the product of Preparation 4 and the product of Preparation 1, the sought product is obtained.

Stage B: 5-methyl-1H-pyrrole-2-carboxylic-3' acid-ester of 2-methylpropyl-7-[(6-deoxy-5-C-methyl-4-O-methyl-alpha-L-lyxo-hexopyranosyl)-oxy]-4-hydroxy-8-methyl-2-oxo-2H-1-benzopyran-3-carboxylate 50 mg of 10% palladium on carbon is added to a solution containing 430 mg of the product prepared in Stage A, 4 ml of ethanol and 3 ml of tetrahydrofuran. Agitation is carried out for 3 hours under a hydrogen atmosphere, followed by filtration. The solvent is evaporated to dryness. The residue is triturated under ultrasound in the presence of isopropyl ether and separated. The product is dried and in this way 279 mg of sought product is obtained.

NMR of the proton (300 MHz, DMSO-$d_6$, ppm) 0.94 (d, 6H, J=6.5 Hz), 1.10 (s, 3H), 1.29 (s, 3H), 1.92 (m, 2H), 2.17 (s, 3H), 2.25 (s, 3H), 3.47 (s, 3H), 3.64 (d, 1H, J=10.0 Hz), 3.89 (d, 2H, J=6.5 Hz), 4.15 (m, 1H), 5.48 (dd, 1H, J=3.0 and 10.0 Hz), 5.54 (ws, 1H), 5.64 (d, 1H, J=5.0 Hz), 5.92 (m, 1H), 6.77 (m, 1H), 6.99 (d, 1H, J=9.0 Hz), 7.76 (d, 1H, J=9.0 Hz), 11.66 (ws, 1H).

EXAMPLE 7

2-methylpropyl-7-((3-O-(aminocarbonyl)-6-deoxy-5-C-methyl-4-O-methyl-alpha-L-lyxo-hexopyranosyl)-oxy]-4-hydroxy-8-methyl-2H-1-benzopyran-3-carboxylate Stage A: 2-methylpropyl-7-[(6-deoxy-5-C-methyl-4-O-methyl-alpha-L-lyxo-hexopyranosyl)-oxy]-8-methyl-2-oxo-4-(phenylmethoxy)-2H-1-benzopyran-3-carboxylate The operation is carried out as in Example 1 Stage A, starting from 6-deoxy-5-C-methyl-4-O-methyl-alpha-L-lyxo-hexopyranose and 2-methylpropyl-7-hydroxy-8-methyl-2-oxo-4-(phenylmethoxy)-2H-1-benzopyran-3-carboxylate, the sought product is obtained. rf=0.22 hexane-ethyl acetate (1-2).

Stage B: 2-methylpropyl-7-[(2,3-O-carbonyl-6-deoxy-5-C-methyl-4-O-methyl-alpha-L-lyxo-hexopyranosyl)-oxy]-8-methyl-2-oxo-4(phenylmethoxy)-2H-1-benzopyran-3-carboxylate A solution containing 700 mg of the product prepared in Stage A, 408 mg of carbonyldiimidazole and 10 ml of THF is taken to reflux. The reaction medium is maintained under reflux for 30 minutes and diluted with 50 ml of a hexane-ethyl acetate mixture (1-2). Washing is carried out with a 1M aqueous solution of sodium dihydrogen phosphate followed by drying, filtering and concentrating to dryness. The product obtained is chromatographed eluting with a hexane-ethyl acetate mixture (1-1). 530 mg of sought product is obtained. rf=0.63 (hexane-ethyl acetate 1-2).

Stage C: 2-methylpropyl-7-[(2,3-O-carbonyl-6-deoxy-5-C-methyl-4-O-methyl-alpha-L-lyxo-hexopyranosyl)-oxy]-4-hydroxy-8-methyl-2-oxo-2H-1-benzopyran-3-carboxylate A mixture containing 4 ml of ethanol, 2 ml of THF and 300 mg of the product prepared in the preceding stage is agitated at ambient temperature for one hour under a hydrogen atmosphere. After filtering, the catalyst is rinsed with THF, the product obtained is evaporated to dryness, triturated under ultrasound in the presence of ethyl ether, followed by separating and drying. 180 mg of product is obtained. rf=0.52 hexane-diethyl acetate (1-1).

Stage D: 2-methylpropyl-7-((3-O-(aminocarbonyl)-6-deoxy-5-C-methyl-4-O-methyl-alpha-L-lyxo-hexopyranosyl)-oxy]-4-hydroxy-8-methyl-2H-1-benzopyran-3-carboxylate 15 ml of liquid ammonia is added to a solution containing 506 mg of the product prepared in Stage C and 3 ml of THF. The ammonia is left to evaporate. The residue is put into solution in a THF-ethyl acetate-hexane mixture (5-3-2). After washing with a 10% solution of sodium hydrogen sulphate, drying and concentrating to dryness, the residue is triturated under ultrasound in the presence of isopropyl ether. After separating and drying 310 mg of sought product is obtained. rf=0.25 $CH_2Cl_3MeOH$ (91-9).

NMR of the proton (400 MHz, DMSO-$d_6$, ppm) 0.98 (d, 6H, J=6.5 Hz), 1.02 (s, 3H), 1.27 (s, 3H), 2.01 (m, 1H), 2.18 (s, 3H), 3.46 (s, 3H), 3.47 (d, 1H, J=10.0 Hz), 3.47 (s, 1H), 4.08 (tl, 1H, J=2.5 Hz), 4.11 (d, 2H, J=6.5 Hz), 5.14 (dd, 1H, J=5 and 10.3 Hz), 5.57 (d, 1H, J=2.5 Hz), 5.63 (s, 1H), 6.61 (ws, 2H), 7.19 (d, 1H, J=9 Hz z), 7.84 (d, 1H, J=9 Hz).

PREPARATION 5

(E) 3-[1-((2-bromoethoxy)imino)ethyl]-7-hydroxy-8-methyl-4-(2-propenyloxy)-2H-1-benzopyran-2-one Stage A: (E) 3-[1-((2-bromoethoxy)imino)ethyl]-4-hydroxy-8-methyl-7-[(tetrahydro-2H-pyran-2-yl)oxy]-2H-1-benzopyran-2-one A mixture of 3.183 g of the product prepared in Stage A of Preparation 7, 4.418 g of bromoethyl O-hydroxylamine hydrobromide and 2.94 g of potassium acetate in 20 $cm^3$ of ethanol is heated to reflux for 1 hour. The ethanol is evaporated off and the residue is dissolved in 100 ml of dichloromethane in the presence 50 ml of an aqueous solution of sodium dihydrogen phosphate. After drying, the methylene chloride is evaporated off, the residue is chromatographed on silica eluting with a hexane-ethyl acetate mixture (2-1). After evaporating the solvents and drying, 2.00 g of product is obtained. rf=0.57 $CH_2Cl_2$—MeOH (94-6).

Stage B: (E) 3-[1-((2-bromoethoxy)imino)-ethyl]-7-hydroxy-8-methyl-4-(2-propenyloxy)-2H-1-benzopyran-2-one 914 $\mu l$ of diethyl azodicarboxylate is added at 0° C. to a solution containing 1.96 g of the product prepared in the preceding stage, 360 ul of allyl alcohol, 1.401 g of triphenylphosphine and 30 ml of dichloromethane. Agitation is carried out for 2 hours at ambient temperature, 180 ul of allyl alcohol, 700 mg of triphenylphosphine and 457 ul of diethyl azodicarboxylate are added at 0° C. Agitation is carried out again for 2 hours at ambient temperature, followed by concentrating and chromatography on silica eluting with a hexane-ethyl acetate mixture (4-1). 2.0 g of product is obtained which is poured into 40 ml of tetrahydrofuran. 20 ml of a 1M aqueous solution of hydrochloric acid is added and agitation is carried out for 2 hours at ambient temperature. After diluting with 30 ml of a hexane-ethyl acetate mixture 1-2, the organic phases are combined, washed with an aqueous solution of sodium dihydrogen phosphate, dried, filtered and concentrated. Trituration is carried out under ultrasound in the presence of a hexane-ethyl acetate mixture (3-1), followed by filtering and drying. 1.17 g of sought product is obtained.

rf=0.28 hexane-ethyl acetate (4-1)

EXAMPLE 8

(E) 5-methyl-1H-pyrrole-2-carboxylic acid-3'-ester of 3-[1-[(2-bromoethoxy)imino]-ethyl]-7-[(6-deoxy-5-C-methyl-4-O-methyl-alpha-L-lyxo-hexopyranosyl)-oxy]-4-hydroxy-8-methyl-2H-1-benzopyran-2-one Stage A: (E) 5-methyl-1H-pyrrole-2-carboxylic acid-3'-ester of 3-[1-((2-bromoethoxy)imino)-ethyl]-7-[(6-deoxy-5-C-methyl-4-O-methyl-alpha-L-lyxo-hexopyranosyl)-oxy]-8-methyl-4-(2-propenyloxy)-2H-1-benzopyran-2-one 580 $\mu l$ of diethyl azodicarboxylate is added dropwise at 0° C. to a mixture containing 1.12 g of the product prepared in Preparation 5, Stage A, 1.015 g of the product of Preparation 1, 890 mg of triphenylphosphine and 15 ml of dichloromethane. Agitation is carried out for 2 hours at ambient temperature and 450 mg of triphenylphosphine and 295 ul of diethyl azodicarboxylate are added. Agitation is carried out for 1 hour, and another 300 mg of triphenylphosphine and 196 $\mu l$ of diethyl azodicarboxylate are added. Agitation is carried out for 1 hour followed by concentrating, chromatographing twice on silica eluting with a hexane-ethyl acetate mixture (2-1).

The solvents are evaporated off and drying is carried out. 862 mg of sought product is obtained.

Stage B: (E) 5-methyl-1H-pyrrole-2-carboxylic acid-3'-ester of 3-[1-[(2-bromoethoxy)imino]-ethyl]-7-[(6-deoxy-5-C-methyl-4-O-methyl-alpha-L-lyxo-hexopyranosyl)-oxy]-4-hydroxy-8-methyl-2H-1-benzopyran-2-one The product is obtained starting from the product prepared in the preceding stage and by operating as in Example 1 Stage C.

rf=0.28 ethyl ether-hexane 2-1

NMR of the proton (300 MHz, DMSO-$d_6$, ppm) 1.08 (s, 3H), 1.30 (s, 3H), 2.24 (s, 3H), 2.25 (s, 3H), 2.28 (s, 3H), 3.47 (s, 3H), 3.65 (d, 1H, J=9.5 Hz), 3.74 (t, 2H, J=5.5 Hz), 4.17 (m, 1H), 4.48 (t, 2H, J=5.5 Hz), 5.48 (dd, 1H, J=3 and 9.5 Hz), 5.64 (d, 1H, J=2.5 Hz), 5.71 (m, 1H), 5.93 (m, 1H), 6.78 (m, 1H), 7.21 (d, 1H, J=9.0 Hz), 7.81 (d, 1H, J=9.0 Hz), 11.66 (ws, 1H), 13.14 (wm, 1H).

EXAMPLE 9

(E) 5-methyl-1H-pyrrole-2-carboxylic acid-3'-ester of 7-[(6-deoxy-5-C-methyl-4-O-methyl-alpha-L-lyxo-hexopyranosyl)oxy]-3-(1-(2-(dimethylamino)ethoxy)imino) ethyl-4-hydroxy-8-methyl-2H-1-benzopyran-2-one 10 mg of tetrabutylammonium iodide, then a solution of 53 mg of 4-dimethylamine in 1 ml of DMF are added to a solution containing 150 mg of the product of Example 8 in 2 ml of anhydrous DMF. The reaction mixture is agitated for 4 hours at ambient temperature, then it is poured into a mixture of 50 ml of THF-AcOEt-Hexane (2-2-1) and 50 ml of water. The aqueous phase is extracted, the organic phases are washed, followed by drying and concentrating to dryness. Trituration is carried out under ultrasound in the presence of isopropyl ether. After separating and drying 55 mg of sought product is obtained.

rf=0.10 $CH_2Cl_2$—$CH_3OH$ (91-9)

NMR of the proton (300 MHz, DMSO-$d_6$, ppm) 1.09 (s, 3H), 1.29 (s, 3H), 2.06 (s, 3H), 2.25 (s, 3H), 2.19 (s, 3H), 2.86 (s, 6H), 3.36 (l, 2H), 3.47 (s, 3H), 3.64 (d, 1H, J=9.5 Hz), 4.15 (m, 1H), 4.34 (l, 2H), 5.48 (dd, 1H, J=2.5 and 9.5 Hz), 5.63 (l, 1H), 5.93 (l, 1H), 6.78 (l, 1H), 7.00 (wm, 1H), 7.75 (wm, 1H).

EXAMPLES 10, 11, 12, 13

By operating as in Example 9, the following products were obtained:

(E) 5-methyl-1H-pyrrole-2-carboxylic acid-3'-ester of 7-[(6-deoxy-5-C-methyl-4-O-methyl-alpha-L-lyxo-hexopyranosyl)oxy]-4-hydroxy-8-methyl-3-(1-((2-(4-morpholinyl)ethoxy) imino)ethyl)-2H-1-benzopyran-2-one rf=0.33 $CH_2Cl_2$—$CH_3OH$ (91-9)

NMR of the proton (300 MHz, DMSO-$d_6$, ppm) 1.10 (s, 3H), 1.30 (s, 3H), 2.03 (s, 3H), 2.19 (s, 3H), 2.22 (s, 3H), 3.25-3.42 (l, 4H), 3.47 (s, 3H), 3.63 (d, 1H, J=9.5 Hz), 4.02 (l, 6H), 4.14 (ws, 1H), 4.34 (l, 2H), 5.48 (dd, 1H, J=3 and 9.5 Hz), 5.54 (d, 1H, J=2 H2), 5.64 (d, 1H, J=4.5 Hz), 5.93 (t, 1H, J=3.0 Hz), 6.77 (t, 1H, J=3.0 Hz), 7.03 (d, 1H, J=8.5 Hz), 7.75 (d, 1H, J=8.5 Hz), 11.66 (ws, 1H).

(E) 5-methyl-1H-pyrrole-2-carboxylic acid-3'-ester of 7-[(6-deoxy-5-C-methyl-4-O-methyl-alpha-L-lyxo-hexopyranosyl)oxy]-4-hydroxy-3-[1-[[2(4hydroxy-1-piperidinyl)ethoxy]imino]ethyl]-8-methyl-2H-1-benzopyran-2-one rf=0.50 $CH_2Cl_2$—$CH_3OH$ (94-6)

NMR of the proton (300 MHz, DMSO-$d_6$, ppm) 1.10 (s, 3H), 1.30 (s, 3H), 1.70-2.25 (m, 4H), 2.02 (s, 3H), 2.19 (s, 3H), 2.24 (s, 3H), 3.34 (m, 6H), 3.47 (s, 3H), 3.63 (d, 1H, J=9.5 Hz), 3.87 (ws, 1H), 4.13 (m, 1H), 4.34 (ws, 2H), 5.00 (s, 1H), 5.48 (dd, 1H, J=3.0 and 9.5 Hz), 5.53 (d, 1H, J=2 Hz), 5.63 (d, 1H, J=5.0 Hz), 5.92 (t, 1H, J=3.0 Hz), 6.78 (t, 1H, J=3.0 Hz), 6.98 (d, 1H, J=9.0 Hz), 7.71 (d, 1H, J=9.0 Hz), 11.66 (ws, 1H).

(E) 5-methyl-1H-pyrrole-2-carboxylic acid-3'-ester of 7-[(6-deoxy-5-C-methyl-4-O-methyl-alpha-L-lyxo-hexopyranosyl)oxy]-4-hydroxy-3-[1-[[2-[(1H-imidazol-2-yl)thio]ethoxy]imino]ethyl]-8-methyl-2H-1-benzopyran-2-one rf=0.20 $CH_2Cl_2$—$CH_3OH$ (94-6)

NMR of the proton (300 MHz, DMSO-$d_6$, ppm) 1.09 (s, 3H), 1.30 (s, 3H) 2.23 (s, 3H), 2.25 (s, 3H), 3.38 (m, 2H), 3.48 (s, 3H), 3.66 (d, 1H, J=9.5 Hz), 4.17 (dd, 1H, J=2.0 and 3.0 Hz), 4.37 (t, 2H, J=5.5 Hz), 5.48 (dd, 1H, J=3.0 and 9.5 Hz), 5.62 (d, 1H, J=2 Hz), 5.93 (t, 1H, J=3.0 Hz), 6.78 (t, 1H, J=3.0 Hz), 7.16 (d, 1H, J=9.0 Hz), 7.21 (s, 2H), 7.82 (d, 1H, J=9.0 Hz), 11.66 (s, 1H).

(E) 5-methyl-1H-pyrrole-2-carboxylic acid-3'-ester of 7-[(6-deoxy-5-C-methyl-4-O-methyl-alpha-L-lyxo-hexopyranosyl)oxy]-4-hydroxy-8-methyl-3-[1-[[2-[(1H-1,2,4-triazol-1-yl)ethoxy]imino]ethyl]-2H-1-benzopyran-2-one rf=0.36 $CH_2Cl_2$—$CH_3OH$ (91-9)

NMR of the proton (300 MHz, DMSO-$d_6$, ppm) 1.07 (s, 3H), 1.30 (s, 3H), 2.14 (s, 3H), 2.25 (s, 3H), 3.47 (s, 3H), 3.66 (d, 1H, J=9.5 Hz), 4.17 (s, 1H), 4.51 (m, 4H), 5.48 (dd, 1H, J=2.5 and 9.5 Hz), 5.64 (d, 1H, J=2 Hz), 5.72 (l, 1H), 5.93 (ws, 1H), 6.78 (t, 1H, J=3.0 Hz), 7.21 (d, 1H, J=9.0 Hz), 7.81 (d, 1H, J=9.0 Hz), 8.01 (s, 1H), 8.54 (s, 1H), 11.66 (l, 1H).

PREPARATION 6

(E) 3-[2-ethoxy-1-(methoxyimino)ethyl]-7-hydroxy-8-methyl-4-(2-propenyloxy)-2H-1-benzopyran-2-one Stage A: (E) 3-(ethoxyacetyl)-4-hydroxy-8-methyl-7-[(tetra-hydro-2H-pyran-2-yl)oxy]-2H-1-benzopyran-2-one 2.21 ml of ethoxy acetic acid is added to a solution containing 5.00 g of 4-hydroxy-8-methyl-7-[(tetrahydro-2H-pyran-2-yl)oxy]-2H-1-benzopyran-2-one, 7.30 g of 4-dimethyl-aminopyridine and 3.816 g of N-(3-dimethylaminopropyl)-N'-ethylcarbodiimide hydrochloride. This mixture is agitated for 16 hours at ambient temperature. After diluting with dichloromethane, washing is carried out with an aqueous solution of sodium dihydrogen phosphate then with brine. After drying over magnesium sulphate, filtering and evaporating to dryness, the product obtained is triturated in a hexane-ethyl acetate mixture (4-1). The product obtained is separated and dried. In this way 5.40 g of sought product is obtained.

Stage B: (E) 3-[2-ethoxy-1-(methoxyimino)ethyl]-4-hydroxy-8-methyl-7-[(tetrahydro-2H-pyran-2-yl)oxy]-2H-1-benzopyran-2-one A mixture of 2 g of the product obtained in the preceding stage, 922 mg of methoxylamine hydrochloride and 1.62 g potassium acetate and 20 ml of ethanol is heated under reflux for 2 hours. The ethanol is evaporated to dryness. The product obtained is chromatographed on silica eluting with a hexane-ethyl acetate mixture (1-1), then with a methylene chloride-methanol mixture 94-6. The solvents are evaporated and drying is carried out. 1.014 g of product is obtained.

rf=0.22 $CH_2Cl_2$—$CH_3OH$ (94-6)

Stage C: (E) 3-[2-ethoxy-1-(methoxyimino)ethyl]-8-methyl-4-(2propenyloxy)-7-[(tetrahydro-2H-pyran-2-yl)oxy]-2H-1-benzopyran-2-one 534 µl of diethyl azodicarboxylate is added to a mixture containing 1 g of the product prepared in the preceding stage, 208 µl of allyl alcohol, 804 mg of triphenylphosphine and 15 ml of dichloromethane. Agitation is carried out for 2 hours at ambient temperature, 402 mg of triphenylphosphine, 104 µl of allyl alcohol and 267 µl of diethyl azodi-carboxylate are added. Agitation is carried out for 2 hours at ambient temperature, followed by concentration under reduced pressure and chromatography on silica eluting with a hexane-ethyl acetate mixture (2-1). The solvents are evaporated, drying is carried out and 672 mg of product is obtained. rf=0.60 hexane-ethyl acetate (1-2).

Stage D: (E) 3-[2-ethoxy-1-(methoxyimino)ethyl]-7-hydroxy-8-methyl-4-(2-propenyloxy)-2H-1-benzopyran-2-one 12 ml of an aqueous solution of hydrochloric acid is added to a solution containing 650 mg of the preceding product in 12 ml of tetrahydrofuran. Agitation is carried out for 6 hours at ambient temperature, followed by diluting with 50 ml of a hexane-ethyl acetate mixture (1-2). After extracting with a hexane-ethyl acetate mixture (1-2), the organic phases are combined, washed with a solution of sodium dihydrogen phosphate; dried, filtered and concentrated to dryness. The residue is triturated under ultrasound in the presence a hexane-ethyl acetate mixture (3-1). After separating and drying, 410 mg of sought product is obtained.

rf=0.50 hexane-ethyl acetate (1-1).

EXAMPLE 14

(E) 5-methyl-1H-pyrrole-2-carboxylic acid-3'-ester of 7-[(6-deoxy-5-C-methyl-4-O-methyl-alpha-L-lyxo-hexopyranosyl)oxy]-3-(2-ethoxy 1-(methoxyimino)ethyl)-4-hydroxy-8-methyl-2H-1-benzopyran-2-one Stage A: (E) 5-methyl-1H-pyrrole-2-carboxylic acid-3'-ester of 7-[(6-deoxy-5-C-methyl-4-O-methyl-alpha-L-lyxo-hexopyranosyl)oxy]-3-[2-ethoxy 1-(methoxyimino)ethyl]-8-methyl-4-(2-propenyloxy)-2H-1-benzopyran-2-one The operation is carried out as in Example 1 Stage 1 starting from the product of Preparation 1 and the product of Preparation 6, the sought product is obtained.

rf=0.41 hexane-ethyl acetate (1-1).

Stage B: (E) 5-methyl-1H-pyrrole-2-carboxylic acid-3'-ester of 7-[(6-deoxy-5-C-methyl-4-O-methyl-alpha-L-lyxo-hexopyranosyl)oxy]-3-(2-ethoxy1-(methoxyimino)ethyl)-4-hydroxy-8-methyl-2H-1-benzopyran-2-one 31 mg of palladium tetrakistriphenylphosphine is added to a solution containing 170 mg of the product prepared in the preceding stage. 188 μl of diisopropylamine and 5 ml of tetrahydrofuran. Agitation is carried out for 20 minutes at 0° C. and the reaction medium is poured into a mixture of 25 ml of a 10% aqueous solution of sodium hydrogen sulphate and 50 ml of a solution of hexane-ethyl acetate (1-4). The organic phase is washed followed by drying, filtering and concentrating to dryness. The residue is chromatographed on silica, eluting with dichloromethane with 5% methanol. The solvents are evaporated off and the residue is triturated under ultrasound, in the presence of ethyl ether. After separating and drying 72 mg of sought product is obtained.

rf=0.41 hexane-ethyl acetate (1-1).

NMR of the proton (300 MNz, DMSO-$d_6$, ppm) 0.96 (t, J=7.0 Hz), 1.03 (t, J=7.0 Hz), 1.08 (s), 1.29 (s), 2.20–2.30 (m), 3.30 (m), 3.47 (s), 3.50 (m), 3.65 (d, J=10 Hz), 3.76 (s), 3.87 (s), 4.16 (m), 4.23 (s), 4.42 (s), 5.48 (dd, J=3 and 10 Hz), 5.60 (m), 5.68 (d, J=5.0 Hz), 5.93 (m), 6.78 (m), 7.10 (d, J=9.0 Hz), 7.16 (d, J=9.0 Hz), 7.77 (d, J=9.0 Hz), 11.65 (ws).

PREPARATION 7

(E) 7-hydroxy-3-[1-(methoxyimino)ethyl]-8-methyl-4-(2-propenyloxy)-2H-1-benzopyran-2-one Stage A: 3-acetyl-4-hydroxy-8-methyl-7-[(tetrahydro-2H-pyran-2-yl)oxy]-2H-1-benzopyran-2-one 2.39 ml of acetic acid is added to a solution containing 10.00 g of the product of Stage B of Preparation 2, 14.59 g of 4-dimethylaminopyridine and 7.63 g of N-(3-dimethylamino-propyl)-N'-ethylcarbodiimide hydrochloride. Agitation is carried out for 5 hours at ambient temperature. Another 4.86 g of 4-dimethylaminopyridine and 3.82 g of N-(3-dimethyl-aminopropyl)-N'-ethylcarbodiimide hydrochloride are added, and agitation is carried out for another 16 hours.

Dilution is carried out with dichloromethane followed by washing with a 10% aqueous solution of sodium hydrogen sulphate, drying, filtering and concentrating to dryness. The residue is triturated under ultrasound in the presence of a hexane-ethyl acetate mixture (2-1). After separating and drying 10.04 g of sought product is obtained. rf=0.79 $CH_2Cl_2$—$CH_3OH$ (95-5).

Stage B: (E) 4-hydroxy-3-[1-(methoxyimino)ethyl]-8-methyl-7-[(tetrahydro-2H-pyran-2-yl)oxy]-2H-1-benzopyran-2-one A mixture of 1.7 g of the product prepared in the preceding stage, 892 mg of methoxyamine hydrochloride. 1.151 g of potassium acetate and 20 ml of ethanol is heated to 80° C. for 30 minutes. After evaporation to dryness the residue is taken up in dichloromethane in the presence of water, followed by washing with an aqueous solution of sodium dihydrogen phosphate (1M), drying, filtering and evaporating to dryness. After trituration under ultrasound in the presence of a hexane-ethyl acetate mixture (4-1) and drying, 1.60 g of product is obtained.

rf=0.28 $CH_2Cl_2$—$CH_3OH$ (99.5-0.5)

Stage C: (E) 3-[1-(methoxyimino)ethyl]-8-methyl-4-(2-propenyloxy)-7-(tetrahydro-2H-pyran-2-yl)oxy]-2H-1-benzopyran-2-one 937 μl of diethyl azodicarboxylate is added at 0° C. to a mixture containing 1.56 g of the product prepared in Stage B. 366 μl of allyl alcohol, 1.413 g of triphenylphosphine and 15 ml of dichloromethane. Agitation is carried out for 2 hours at ambient temperature. 706 mg of triphenylphosphine, 183 μl of allyl alcohol and 468 μl of diethyl azodicarboxylate are added. Agitation is carried out for another 2 hours at ambient temperature. The reaction mixture is concentrated and chromatographed on silica eluting with a hexane-ethyl acetate mixture(4-1). The solvents are evaporated and drying is carried out. 1.00 g of sought product is obtained.

rf=0.38 hexane-ethyl acetate (4-1).

Stage D: (E) 7-hydroxy-3-[1-(methoxyimino)ethyl]-8-methyl-4-(2-propenyloxy)-2H-1-benzopyran-2-one 10 ml of a 1M aqueous solution of hydrochloric acid is added to a solution containing 1 g of the product prepared in Stage C and 20 ml of tetrahydrofuran. Agitation is carried out for 7 hours at ambient temperature followed by dilution with 50 ml of a hexane-ethyl acetate mixture (1-1). The phases are separated and the aqueous phase is extracted with a hexane-ethyl acetate mixture (1-1). The organic phases are combined and washed with a 1M solution of sodium dihydrogen phosphate, followed by drying, filtering and concentrating to dryness. The residue is triturated with a hexane-ethyl acetate mixture (4-1). After separating and drying 770 mg of product is collected.

EXAMPLE 15

(E) 5-methyl-1H-pyrrole-2-carboxylic acid-3'-ester of 7-[(6-deoxy-5-C-methyl-4-O-methyl-alpha-L-lyxo-hexopyranosyl)oxy]-4-hydroxy-3-(1-(methoxyimino)ethyl)-8-methyl-2H-1-benzopyran-2-one Stage A: (E) 5-methyl-1H-pyrrole-2-carboxylic acid-3'-ester of 7-[(6-deoxy-5-C-methyl-4-O-methyl-alpha-L-lyxo-hexopyranosyl)oxy]-3-[1-(methoxyimino)ethyl]-8-methyl-4-(2-propenyloxy)-2H-1-benzopyran-2-one The operation is carried out as in Example 1, starting from 455 mg of the product prepared in Preparation 7 and 539 mg of the product of Preparation 1, the sought product is obtained.

rf=0.33 eluant hexane-ethyl acetate (1-1).

Stage B: (E) 5-methyl-1H-pyrrole-2-carboxylic acid-3'-ester of 7-[(6-deoxy-5-C-methyl-4-O-methyl-alpha-L-lyxo-hexopyranosyl)oxy]-4-hydroxy-3-(1-(methoxyimino)ethyl)-8-methyl-2H-1-benzopyran-2-one 460 µl of diisopropylamine then 75 mg of palladium tetrakistriphenylphosphine is added at 0° C. to 6 ml of tetrahydrofuran and 380 mg of the product of the preceding stage. Agitation is carried out for 20 minutes at 0° C. and the reaction medium is poured into a mixture of a 10% solution of sodium hydrogen sulphate and tetrahydrofuran-hexane-ethyl acetate (1-1-1). The phases are separated, the aqueous phase is extracted with a tetrahydrofuran-hexane-ethyl acetate mixture (1-1-1). The organic phases are combined, dried, filtered and concentrated to dryness. The residue is triturated under ultrasound in the presence of isopropyl ether. After separating and drying under reduced pressure 180 mg of sought product is obtained.

rf=0.35 $CH_2Cl_2$—$H_3OH$ (94-6)

NMR of the proton (300 MHz, DMSO-$d_6$, ppm) 1.08 (s, 3H), 1.30 (s, 3H), 2.23 (s, 3H), 2.25 (s, 3H), 2.27 (s, 3H), 3.47 (s, 3H), 3.65 (d, 1H, J=10.0 Hz), 3.95 (s, 3H), 4.17 (m, 1H), 5.48 (dd, 1H, J=3.0 and 10.0 Hz), 5.63 (d, 1H, J=2.5 Hz), 5.70 (d, 1H, J=5.0 Hz), 5.93 (m, 1H), 6.78 (m, 1H), 7.20 (d, 1H, J=9.0 Hz), 7.80 (d, 1H, J=9.0 Hz), 11.65 (ws, 1H), 13.69 (ml, 1H).

PREPARATION 8

(E) 7-hydroxy-3-[(methoxyimino)methyl]-8-methyl-4-(2-propenyloxy)-2H-1-benzopyran-2-one Stage A: 4-hydroxy-8-methyl-2-oxo-7-[(tetrahydro-2H-pyran-2-yl)oxy]-2H-1-benzopyran-3-carboxaldehyde 700 µl of formic acid is added at ambient temperature to a solution containing 75 ml of dichloromethane, 5.0 g of the product prepared in Stage B of Preparation 2, 6.625 g of 4-dimethylaminopyridine and 3.825 g of N-(3-dimethylaminopropyl)-N'-ethylcarbodiimide. Agitation is carried out for 16 hours, followed by diluting with dichloromethane, washing with a 10% aqueous solution of sodium hydrogen sulphate then with a 1M solution, drying, filtering and evaporating to dryness. After trituration under ultrasound in the presence ether, separating and drying 4.04 g of sought product is collected.

Stage B: (E) 4-hydroxy-3-[(methoxyimino)methyl]-8-methyl-7-[(tetrahydro-2H-pyran-2-yl)oxy]-2H-1-benzopyran-2-one A mixture containing 2.0 g of the product prepared in Stage A, 1.08 g of methoxyamine hydrochloride, 1.93 g of potassium acetate and 20 ml of ethanol is heated under reflux for 1 hour. After evaporating to dryness, the product obtained is dissolved in a mixture of dichloromethane and water (100 ml–100 ml), washed with a dilute solution of sodium acid phosphate and dried. After evaporation, the residue is triturated under ultrasound in the presence of ethyl ether, separated and dried. 1.90 g of product is obtained.

Stage C: (E) 3-[(methoxyimino)methyl]-8-methyl-4-(2-propenyloxy)—7-[(tetrahydro-2H-pyran-2-yl)oxy]-2H-1-benzopyran-2-one 1.02 ml of diethyl azodicarboxylate is added at 0° C. to a mixture containing 1.80 g of the product prepared in the preceding stage, 441 µl of allyl alcohol, 1.70 g of triphenylphosphine and 15 ml of dichloromethane. Agitation is carried out for 2 hours at ambient temperature. 845 mg of triphenylphosphine, 220 µl of allyl alcohol and 564 µl of DEAD are added at 0° C. Agitation is carried out for 2 hours, followed by concentration under reduced pressure and chromatography on silica eluting with a hexane-ethyl acetate mixture (3-1). The solvents are evaporated off and after drying 1.60 g of product is obtained.

Stage D: (E) 7-hydroxy-3-[(methoxyimino)methyl]-8-methyl-4-(2-propenyloxy)-2H-1-benzopyran-2-one 20 ml of a 1M aqueous solution of hydrochloric acid is added to a solution containing 1.60 g of the product prepared in the preceding stage and 20 ml of THF. Agitation is carried out for 6 hours at ambient temperature. The reaction solution is diluted with 30 ml of a hexane-ethyl acetate mixture (1-2). The phases are separated and the aqueous phase is extracted with a hexane-ethyl acetate mixture (1-2). The organic phases are washed with a 1M solution of sodium dihydrogen phosphate, dried, filtered and concentrated to dryness. The residue is triturated under ultrasound in the presence of hexane-ethyl acetate (3-1). After separating and drying 920 mg of sought product is obtained. rf=0.47 hexane-ethyl acetate (1-2).

EXAMPLE 16

(E) 5-methyl-1H-pyrrole-2-carboxylic acid-3'-ester of 7-[(6-deoxy-5-C-methyl-4-O-methyl-alpha-L-lyxo-hexopyranosyl)oxy]-4-hydroxy-8-methyl-3-(methoxyimino)methyl)-2H-1-benzopyran-2-one Stage A: (E) 5-methyl-1H-pyrrole-2-carboxylic acid-3'-ester of 7-[(6-deoxy-5-C-methyl-4-O-methyl-alpha-L-lyxo-hexopyranosyl)oxy]-3-[(methoxyimino)methyl]-8-methyl-4-(2-propenyloxy)-2H-1-benzopyran-2-one The operation is carried out as in Example 1, starting from the product of Preparation 8 and the product of Preparation 1, the sought product is obtained.

rf=0.34 hexane-ethyl acetate (1-1)

Stage B: (E) 5-methyl-1H-pyrrole-2-carboxylic acid-3'-ester of 7-[(6-deoxy-5-C-methyl-4-O-methyl-alpha-L-lyxo-hexopyranosyl)oxy]-4-hydroxy-8-methyl-3-(methoxyimino)methyl)-2H-1-benzopyran-2-one 87 mg of palladium tetrakistriphenylphosphine is added at 0° C. to a solution containing 430 mg of the product prepared in Stage A, 533 µl of diisopropylamine and 10 ml of anhydrous tetrahydrofuran. Agitation is carried out for 20 minutes at 0° C., the reaction mixture is poured into 50 ml of an aqueous solution of sodium hydrogen sulphate and 50 ml of a hexane-ethyl acetate mixture (1-2). Washing is carried out followed by drying, filtering and concentrating to dryness. After chromatography on silica, eluting with a methylene chloride-methanol mixture 95-5, the solvents are evaporated off, the residue is triturated under ultrasound in the presence of ethyl ether. After separating and drying 176 mg of sought product is obtained.

rf=0.34 hexane-ethyl acetate 1-1.

NMR of the proton (300 MHz, DMSO-$d_6$, ppm) 1.08 (s, 3H), 1.30 (s, 3H), 2.22 (s, 3H), 2.25 (s, 3H), 3.47 (s, 3H), 3.65 (d, 1H, J=10.0 Hz), 3. 90 (s, 3H), 4.16 (m, 1H), 5.48 (dd, 1H, J=3.0 and 10.0 Hz), 5.61 (d, 1H, J=2.0 Hz), 5.70 (d, 1H, J=5.0 Hz), 5.93 (m, 1H), 6.78 (m, 1H), 7.16 (d, 1H, J=9.0 Hz), 7.78 (d, 1H, J=9.0 Hz), 8.35 (s, 1H), 11.66 (ws).

EXAMPLE 17 cyclopropyl-carbamic acid-3'-ester of 3-acetyl-7-[(6-deoxy-5-C-methyl-4-O-methyl-alpha-L-lyxo-hexopyranosyl)oxy]-4-hydroxy-8-methyl-2H-1-benzopyran-2-one Stage A: 7-[(6-deoxy-5-C-methyl-4-O-methyl-alpha-L-lyxo-hexopyranosyl)oxy]-8-methyl-4-(2-propenyloxy)-2H-1-benzopyran-2-one 8.10 ml of diethyl azodicarboxylate is added dropwise to a mixture containing 8.50 g of the product of Preparation 2, 8.44 g of 6-deoxy 5-C-methyl-4-O-methyl-L-lyxo-hexopyranose. 11.52 g of triphenylphosphine, 100 ml of dichloromethane and 20 ml of tetrahydrofuran. The reaction medium is maintained under agitation for 2 hours at ambient temperature and 5.70 g of triphenylphosphine and 4.05 ml of diethyl azodicarboxylate are added. Agitation is maintained overnight at ambient temperature. After concentrating, the product is purified by chromatography on silica, eluting with a methylene chloride-acetone mixture (90-10). After evaporation and drying 8.304 g of sought product is collected.

Stage B: 7-[(2,3-O-carbonyl-6-deoxy-5-C-methyl-4-O-methyl-alpha-L-lyxo-hexopyranosyl)oxy]-8-methyl-4-(2-propenyloxy)-2H-1-benzopyran-2-one A mixture of 2 g of the product prepared in Stage A and 1.995 g of carbonyldiimidazole is heated under reflux for 30 minutes. The reaction medium is cooled down and diluted with 100 ml of a tetrahydrofuran-ethyl acetate mixture (1-1). After washing water, drying, filtering and concentrating the residue is dissolved in dichloromethane then chromatography is carried out on silica eluting with a methylene chloride-acetone mixture (9-1). The solvents are evaporated off and 1.32 g of sought product is obtained.

rf=0.69 $CH_2Cl_2$—$CH_3COCH_3$ (90-10).

Stage C: 7-[(2,3-O-carbonyl-6-deoxy-5-C-methyl-4-O-methyl-alpha-L-lyxo-hexopyranosyl)oxy]-4-hydroxy-8-methyl-2H-1-benzopyran-2-one 1 ml of isopropylamine is added to a mixture containing 1 g of the product prepared in the preceding stage and 10 ml of tetrahydrofuran. 267 mg of palladium tetrakistriphenylphosphine is added. Agitation is carried out for 30 minutes at 0° C., 10 ml of sulphuric ether is added followed by filtering. A product is obtained which is filtered, separated and rinsed with an ethyl ether-tetrahydrofuran mixture (1-1). After drying 880 mg of product is obtained which is poured into 75 ml of a tetrahydrofuran-ethyl acetate-hexane mixture (2-2-1). The aqueous phase is extracted with the mixture of solvents. The organic phases are combined, dried, filtered and concentrated. 726 mg of sought product is obtained.

Stage D: 3-acetyl 7-[(2,3-O-carbonyl-6-deoxy-5-C-methyl-4-O-methyl-alpha-L-lyxo-hexopyranosyl)oxy]-4-hydroxy-8-methyl-2H-1-benzopyran-2-one 225 μl of acetic acid is added to a solution containing 1.29 g of the product obtained in Stage C, 1.344 g of 4-dimethylaminopyridine and 719 mg of N-(3-dimethylaminopropyl)-N'-ethyl carbodiimide hydrochloride and 15 ml of dichloromethane. Agitation is carried out for 6 hours at ambient temperature followed by dilution with 50 ml of dichloromethane, washing with a 10% aqueous solution of sodium hydrogen sulphate and drying. The solvents are evaporated off and chromatography is carried out on silica eluting with a methylene chloride-methanol mixture (98-2). The solvents are evaporated off and after drying 1.18 g of sought product is obtained. rf=0.73 methylene chloride-methanol (94-6).

Stage E: cyclopropyl-carbamic acid-3'-ester of 3-acetyl-7-[(6-deoxy-5-C-methyl-4-O-methyl-alpha-L-lyxo-hexopyranosyl)oxy]-4-hydroxy-8-methyl-2H-1-benzopyran-2-one 783 μl of DBUt and 362 ul of cyclopropylamine are added to a solution containing 1.137 g of the product prepared in the preceding stage and 5 ml of dimethylformamide. The reaction medium is maintained under agitation for 3 hours and 181 μl of cyclopropylamine is added. Agitation is carried out for 3 hours followed by pouring the reaction medium into 80 ml of a hexane-ethyl acetate mixture 1-2, in the presence of an aqueous solution of sodium hydrogen sulphate.

Extracted is carried out with a hexane-ethyl acetate mixture (1-2). The organic phases are combined, washed, dried and filtered. After evaporation, the residue is dried. 1.040 g of sought product is obtained. rf=0.58 $CH_2Cl_2$—MeOH (90-10).

NMR of the proton (300 MHz, DMSO-$d_6$, ppm) ~0.43 (m, 2H), 0.60 (m, 2H), 1.04 (s, 3H), 1.18 (s, 3H), 2.19 (s, 3H), 2.65 (s, 3H), 3.12 (m, 1H), 3.45 (s, 3H), ~3.49 (m, 1H), ~4.02 (ws, 1H), 5.18 (dd, 1H, J=3.0 and 10.0 Hz), 5.60 (ws, 1H), 7.21 (d, 1H, J=9.0 Hz), 7.50 (ws, 1H), 7.90 (d, 1H, J=9.0 Hz), 13.75 (ws, 1H).

EXAMPLE 18

(E) cyclopropyl-carbamic acid-3'-ester of 7-[(6-deoxy-5-C-methyl-4-O-methyl-alpha-L-lyxo-hexopyranosyl)oxy]-4-hydroxy-3-(1-(methoxyimino)ethyl)-methyl-2H-1-benzopyran-2-one A mixture containing 100 mg of the product prepared in the preceding example, 34 mg of methoxylamine hydrochloride, 50 mg of potassium acetate and 2 ml of ethanol is heated under reflux for 1 hour. The ethanol is evaporated to dryness and the residue is taken up in 40 ml of dichloromethane. Washing is carried out with a 1M aqueous solution of sodium dihydrogen phosphate and followed by drying over magnesium sulphate. The solvent is evaporated off and chromatography is carried out on preparative plates. After extraction, the solvents are evaporated off then the product obtained is dissolved in ethyl ether and n-pentane is added. The product obtained is separated and dried. 56 mg of sought product is obtained. rf=0.41 $CH_2Cl_2$—MeOH (94-6).

NMR of the proton (300 MHz, DMSO-$d_6$, ppm) 0.44 (m, 2H), 0.60 (m, 2H), 1.04 (s, 3H), 1.26 (s, 3H), 2.20, (s, 3H), 2.27 (s, 3H), 3.45 (m, 1H), 3.45 (s, 3H), 3.95 (s, 3H), 4.09 (m, 1H), 5.19 (dd, 1H, J=3.0 and 10.0 Hz), 5.55 (ws, 1H), 5.64 (d, 1H, J=5.0 Hz), 7.16 (d, 1H, J=9.0 Hz), 7.51 (m, 1H), 7.79 (d, 1H, J=9.0 Hz), 13.67 (ml, 1H)

EXAMPLE 19

(E) cyclopropyl-carbamic acid-3'-ester of 7-[(6-deoxy-5-C-methyl-4-O-methyl-alpha-L-lyxo-hexopyranosyl)oxy]-3-(1-dimethylhydrazono)ethyl)-4-hydroxy-8-methyl-2H-1-benzopyran-2-one The operation is carried out as in the preceding example using $Me_2N$—$NH_2$ instead off $NH_2OMe.HCl$, the sought product is obtained NMR of the proton (300 MHz, DMSO-$d_6$, ppm) 0.43 (m, 2H), 0.60 (m, 2H), 1.04 (s, 3H), 1.25 (s, 3H), 2.16 (s, 3H), 2.68 (s, 6H), 2.76 (s, 3H), 3.44 (s, 3H), 3.48 (d, 1H, J=10.0 Hz), 4.07 (ws, 1H), 5.18 (dd, 1H, J=3.0 and 10.0 Hz), 5.51 (ws, 1H), 5.61 (d, 1H, J=5.0 Hz), 7.05 (d, 1H, J=9.0 Hz), 7.50 (ws, 1H), 7.78 (d, 1H, J=9.0 Hz), 14.50 (ws, 1H).

EXAMPLE 20 ethyl 7-[(6-deoxy-5-C-methyl-4-O-methyl-3-O-(((5-methyl-3-isoxazolyl)amino)-carbonyl)-alpha-L-lyxo-hexopyranosyl)oxy]-4-hydroxy-8-methyl-2-oxo-2H-1-benzopyran-3-carboxylate Stage A: ethyl 7-[(2,3-O-carbonyl-6-deoxy-5-C-methyl-4-O-methyl-alpha-L-lyxo-hexopyranosyl)oxy]-8-methyl-2-oxo-4-(phenylmethoxy)-2H-1-benzopyran-3-carboxylate 5.33 ml of diisopropylazodicarboxylate is added at 0° C. to a mixture containing 8.00 g of the product of Preparation 3, 5.207 g of 6-deoxy 5-C-methyl-4-O-methyl-L-lyxo-hexopyranose and 50 ml of dichloromethane. Agitation is carried out for 2 hours at ambient temperature. 3.6 g of triphenylphosphine and 2.7 ml of azodicarboxylate is added and agitation is carried out for 2 hours. The reaction medium is concentrated and chromatography is carried out on silica eluting with a hexane-ethyl acetate mixture (2-3). 8.43 g of product is obtained which is poured into 70 ml of tetrahydrofuran. 5.17 g of carbonyldiimidazole is added and the reaction medium is heated under reflux for 30 minutes. The solution is cooled down and diluted with 100 ml of a hexane-ethyl acetate mixture (1-2) followed by washing with an aqueous solution of sodium dihydrogen phosphate, drying, filtering and evaporating the solvents. The product obtained is chromatographed on silica eluting with a hexane-ethyl acetate mixture (1-1). After evaporating the solvents and drying, 6.48 g of sought product is obtained.

Stage B: ethyl 7-[(2,3-O-carbonyl-6-deoxy-5-C-methyl-4-O-methyl-alpha-L-lyxo-hexopyranosyl)oxy]-4-hydroxy-8-methyl-2-oxo-2H-1-benzopyran-3-carboxylate 600 mg of 10% palladium on carbon is added a solution containing 6.00 g of the product prepared in Stage A, 30 ml of ethanol and 15 ml of tetrahydrofuran. This mixture is agitated under hydrogen pressure for 6 hours, followed by filtering and rinsing with THF. The solvents are evaporated and drying is carried out. 4.572 g of sought product is obtained. rf=0.59 $CH_2Cl_2$—MeOH (91-9).

Stage C: ethyl-7-[(6-deoxy-5-C-methyl-4-O-methyl-3-O-(((5-methyl-3-isoxazolyl)amino)-carbonyl)-alpha-L-lyxo-hexopyranosyl)-oxy]-4-hydroxy-8-methyl-2-oxo-2H-1-benzopyran-3-carboxylate A solution containing 254 mg of 5-methylaminoisoxazole and 2 ml of anhydrous tetrahydrofuran is cooled down to −76° C. 1.08 ml of 1.6 M n-butyllithium in hexane is added at −76° C. The reaction mixture is maintained under agitation for 15 minutes. A solution of 400 mg of the product prepared in the preceding stage in 2 ml of THF is added. The reaction mixture is maintained under agitation at −76° C. for 2 hours then at −20° C. for 40 minutes. Dilution is carried out with 150 ml of ethyl acetate with 20% hexane, followed by washing with 70 ml of a 10% aqueous solution of sodium acid sulphate, with water and with brine, drying and evaporating to dryness after filtration. 504 mg of product is collected which is solubilized in the minimum amount of dichloromethane containing 10% methanol. Chromatography is carried out on silica eluting with a methylene chloride-ethanol mixture 10%. After evaporation of the solvents, 264 mg of product is obtained which is chromatographed on silica eluting with a methylene chloride-methanol mixture (94-6). 145 mg of product is obtained. The sought product is obtained. rf=0.21 $CH_2Cl_2$—$CH_3OH$ (95-5).

NMR of the proton (300 MHz, DMSO-$d_6$, ppm) 1.05 (s, 3H), 1.28 (m, 3H), 1.28 (m, 3H), 2.19 (s, 3H), 2.37 (s, 3H), 3.49 (s, 3H), 3.57 (d, 1H, J=10.0 Hz), 4.19 (ws, 1H), 4.32 (q, 2H, J=7.0 Hz), 5.25 (dd, 1H, J=3.0 and 10.0 Hz), 5.61 (ws, 1H), 5.83 (s, 1H), 6.56 (s, 1H), 7.16 (d, 1H, J=9.0 Hz), 7.83 (d, 1H, 9.0 Hz).

By operating as in the preceding example starting from the product prepared in Stage B of the preceding example and the corresponding amines, the following products were obtained:

EXAMPLE 21 ethyl 7-[(6-deoxy-5-C-methyl-4-O-methyl-3-O-(((2-thiazolyl)amino)carbonyl)-alpha-L-lyxo-hexopyranosyl)oxy]-4-hydroxy-8-methyl-2-oxo-2H-1-benzopyran-3-carboxylate rf=0.07 $CH_2Cl_2$—$CH_3OH$ (95-5)

NMR of the proton (300 MHz, DMSO-$d_6$, ppm) 1.07 (s, 3H), 1.25 (t, 3H, J=7.0 Hz), 1,29 (s, 3H), 2.18 (s, 3H), 3.51 (s, 3H), 3.57 (d, 1H, J=10.0 Hz), 4.21 (m, 3H), 5.28 (dd, 1H, J=3.0 and 10.0 Hz), 5.57 (ws, 1H), 5.80 (d, 1H, J=5.0 Hz), 7.05 (dl, 1H, J=9.0 Hz), 7.77 (d, 1H, J=9.0 Hz), 7.22 (d, 1H, J=3.5 Hz), 7.42 (d, 1H, J=3.5 Hz z), 11.95 (ws, 1H).

EXAMPLE 22 ethyl 7-[(6-deoxy-5-C-methyl-4-O-methyl-3-O-(((phenylmethyl)amino)carbonyl)-alpha-L-lyxo-hexopyranosyl)oxy]-4-hydroxy-8-methyl-2-oxo-2H-1-benzopyran-3-carboxylate rf=0.30 $CH_2Cl_2$—$CH_3OH$ (95-5)

NMR of the proton (300 MHz, DMSO-$d_6$, ppm) 1.02 (s, 3H), 1.27 (s, 3H), 1.32 (t, 3H, J=7.0 Hz), 2.17 (s, 3H), 3.48 (s, 3H), 3.51 (d, 1H, J=10.0 Hz), 4.11 (ws, 1H), 4.21 (m, 2H), 4.37 (q, 2H, J=7.0 Hz), 5.22 (dd, 1H, J=3.0 and 10.0 Hz), 5.59 (d, 1H, J=2.0 Hz), 5.71 (l, 1H), 7.21 (d, 1H, J=9.0 Hz), 7.30 (ml, 5H), 7.85 (d, 1H, J=9.0 Hz), 7.92 (t, 1H, J=6.0 Hz).

EXAMPLE 23 ethyl 7-[(3-O-(((cyclopentyl)amino)carbonyl)-6-deoxy—5-C-methyl-4-O-methyl-alpha-L-lyxo-hexopyranosyl)oxy]-4-hydroxy-8-methyl-2-oxo-2H-1-benzopyran-3-carboxylate rf=0.32 $CH_2Cl_2$—$CH_3OH$ (95-5)

NMR of the proton (300 MHz, DMSO-$d_6$, ppm) 1.26 (s, 3H), 1.32 (s, 3H), 1.32 (t, 3H, J=7.0 Hz), 1.40-1.90 (m, 8H), 2.18 (s, 3H), 3.46 (s, 3H), 3.50 (d, 1H, J=10.0 Hz), 3.82 (m, 1H), 4.08 (l, 1H), 4.32 (q, 2H, J=7.0 Hz), 5.19 (dd, 1H, J=3.0 and 10.0 Hz), 5.58 (ws, 1H), 5.64 (l, 1H), 7.18 (d, 1H, J=9.0 Hz), 7.33 (d, 1H, J=7.0 Hz), 7.85 (d, 1H, J=9.0 Hz).

EXAMPLE 24 ethyl 7-[(3-O-(aminocarbonyl)-6-deoxy-5-C-methyl-4-O-methyl-alpha-L-lyxo-hexopyranosyl)oxy]-4-hydroxy-8-methyl-2-oxo-2H-1-benzopyran-3-carboxylate rf=0.06 $CH_2Cl_2$—$CH_3OH$ (95-5)

NMR of the proton (300 MHz, DMSO-$d_6$, ppm) 1.03 (s, 3H), 1.26 (s, 3H), 1.32 (t, 3H, J=7.0 Hz), 2.18 (s, 3H), 3.47 (s, 3H), 3.48 (l, 1H), 4.08 (dd, 1H, J=2.5 and 3.0 Hz), 4.37 (q, 2H, J=7.0 Hz), 5.15 (dd, 1H, J=3.0 and 10.0 Hz), 5.58 (d, 1H, J=2.5 Hz), 6.55-6.75 (l, 2H), 7.19 (d, 1H, J=9.0 Hz), 7.85 (d, 1H, J=9.0 Hz).

EXAMPLE 25 ethyl 7-[(6-deoxy-5-C-methyl-4-O-methyl-3-O-(((2-pyridinylmethyl)amino)carbonyl)-alpha-L-lyxo-hexopyranosyl)oxy]-4-hydroxy-8-methyl-2-oxo-2H-1-benzopyran-3-carboxylate rf=0.11 $CH_2Cl_2$—$CH_3OH$ (95-5)

NMR of the proton (300 MHz, DMSO-$d_6$, ppm) 1.02 (s, 3H), 1.28 (s, 3H), 1.32 (t, 3H, J=7.0 Hz), 2.16 (s, 3H), 3.50 (s, 3H), 3.54 (d, 1H, J=10.0 Hz), 4.11 (ws, 1H), 4.36 (m, 4H), 5.22 (dd, 1H, J=3.0 and 10.0 Hz), 5.60 (d, 1H, J=2.0 Hz), 5.73 (l, 1H), 7.19 (d, 1H, J=9.0 Hz), 7.29 (t, 1H, J=6.0 Hz), 7.36 (d, 1H, J=8.0 Hz), 7.83 (m, 2H), 7.97 (t, 1H, J=6.0 Hz), 8.22 (m, 1H).

EXAMPLE 26 ethyl 7-[(3-O-(cyclopropylamino)carbonyl)-6-deoxy-5-C-methyl-4-O-methyl-alpha-L-lyxo-hexopyranosyl)oxy]-4-hydroxy-8-methyl-2-oxo-2H-1-benzopyran-3-carboxylate rf=0.32 $CH_2Cl_2$—$CH_3OH$ (92-8)

NMR of the proton (300 MHz, DMSO-$d_6$, ppm) 0.43 (m, 2H), 0.59 (m, 2H), 1.03 (s, 3H), 1.26 (s, 3H), 1.32 (t, 3H, J=7.0 Hz), 2.19 (s, 3H), 3.45-3.48 (m, 2H), 3.44 (s, 3H), 4.09 (ws, 1H), 4.37 (q, 2H, J=7.0 Hz), 5.17 (dl, 1H, J=10.0 Hz), 5.58 (ws, 1H), 5.65 (m, 1H), 7.19 (d, 1H, J=9.0 Hz), 7.50 (ws, 1H), 7.85 (d, 1H, J=9.0 Hz).

EXAMPLE 27 ethyl 7-[(3-O-((cyclobutylamino)carbonyl)-6-deoxy-5-C-methyl-4-O-methyl-alpha-L-lyxo-hexopyranosyl)oxy]-4-hydroxy-8-methyl-2-oxo-2H-1-benzopyran-3-carboxylate rf=0.38 $CH_2Cl_2$—$CH_3OH$ (92-8)

NMR of the proton (300 MHz, DMSO-$d_6$, ppm) 1.01 (s, 3H), 1.26 (s, 3H), 1.32 (t, 3H, J=7.0 Hz), 1.58 (m, 2H), 1.93 (m, 2H), 2.15 (m, 2H), 2.17 (s, 3H), 3.46 (s, 3H), 3.28 (d, 1H, J=10.0 Hz), 4.00 (m, 1H), 4.07 (ws, 1H), 4.36 (q, 2H, J=7.0 Hz), 5.15 (dd, 1H, J=3.0 and 10.0 Hz), 5.57 (d, 1H, J=2.0 Hz), 5.67 (m, 1H), 7.18 (d, 1H, J=9.0 Hz), 7.63 (d, 1H, J=8.0 Hz), 7.85 (d, 1H, J=9.0 Hz).

EXAMPLE 28 ethyl 7-[(6-deoxy-5-C-methyl-4-O-methyl-3-O-(((1-methylethyl)amino)carbonyl)-alpha-L-lyxo-hexopyranosyl)oxy]-4-hydroxy-8-methyl-2-oxo-2H-1-benzopyran-3-carboxylate rf=0.30 $CH_2Cl_2$—$CH_3OH$ (92-8)

NMR of the proton (300 MHz, DMSO-$d_6$, ppm) 1.03 (s, 3H), 1.09 (d, 6H, J=6.5 Hz), 1.26 (s, 3H), 1.32 (t, 3H, J=7.00 Hz), 2.18 (s, 3H), 3.46 (s, 3H), 3.50 (d, 1H, J=10.0 Hz), 3.67 (m, 1H), 4.08 (ws, 1H), 4.37 (q, 2H, J=7.0 Hz), 5.19 (dd, 1H, J=3.0 and 10.0 Hz), 5.58 (d, 1H, J=2.0 Hz), 5.65 (ws, 1H), 7.18 (d, 1H, J=9.0 Hz), 7.22 (d, 1H, J=7.5 Hz), 7.85 (d, 1H, J=9.0 Hz).

EXAMPLE 29 ethyl 7-[(6-deoxy-3-O-(((1,1-dimethylethyl)amino)carbonyl)-5-C-methyl-4-O-methyl-alpha-L-lyxo-hexopyranosyl)oxy]-4-hydroxy-8-methyl-2-oxo-2H-1-benzopyran-3-carboxylate rf=0.37 $CH_2Cl_2$—$CH_3OH$ (92-8)

NMR of the proton (300 MHz, DMSO-$d_6$, ppm) 1.02 (s, 3H), 1.26 (s, 12H), 1.32 (t, 3H, J=7.0 Hz), 2.19 (s, 3H), 3.46 (s, 3H), 4.06 (ws, 1H), 4.37 (q, 2H, J=7.0 Hz), 5.17 (dd, 1H, J=3.0 and 10.0 Hz), 5.58 (d, 1H, J=2.5 Hz), 5.62 (ws, 1H), 7.03 (ws, 1H), 7.19 (d, 1H, J=9.0 Hz), 7.85 (d, 1H, J=9.0 Hz).

EXAMPLE 30 ethyl 7-[(3-O-((cyclohexylamino)carbonyl)-6-deoxy—5-C-methyl-4-O-methyl-alpha-L-lyxo-hexopyranosyl)oxy]-4-hydroxy-8-methyl-2-oxo-2H-1-benzopyran-3-carboxylate rf=0.33 $CH_2Cl_2$—$CH_3OH$ (92-8)

NMR of the proton (300 MHz, DMSO-$d_6$, ppm) 1.00–1.80 (m, 10H), 1.03 (s, 3H), 1.26 (s, 3H), 1.32 (t, 3H, J=7.0 Hz), 2.18 (s, 3H), 3.46 (s, 3H), 3.63 (d, 1H, J=10.0 Hz), 4.08 (ws, 1H), 4.37 (q, 2H, J=7.0 Hz), 5.20 (dd, 1H, J=3.0 and 10.0 Hz), 5.61 (d, 1H, J=2.0 Hz), 5.65 (ws, 1H), 7.19 (d, 1H, J=9.0 Hz), 7.25 (d, 1H, J=8.0 Hz), 7.86 (d d, 1H, J=9.0 Hz).

EXAMPLE 31 ethyl 7-[(6-deoxy-5-C-methyl-4-O-methyl-3-O-((4-methyl-1-piperazinyl)carbonyl)-alpha-L-lyxo-hexopyranosyl)oxy]-4-hydroxy-8-methyl-2H-1-benzopyran-3-carboxylate rf=0.22 $CH_2Cl_2$—$CH_3OH$ (85-15)

NMR of the proton (300 MHz, DMSO-$d_6$, ppm) 1.02 (s, 3H), 1.20 (t, 3H, J=7.0 Hz), 1.30 (s, 3H), 2.12 (s, 3H), 2.60 (ws, 3H), 3.04 (l, 8H), 3. 44 (s, 3H), 3.54 (d, 1H, J=10 Hz), 4.05 (m, 3H), 5.4 (dd, 1H, J=3 and 10 Hz), 5.50 (d, 1H, J=2.0 Hz), 5.62 (d, 1H, J=4.5 Hz), 6.93 (d, 1H, J=9.0 Hz), 7.65 (d, 1H, J=9.0 Hz).

EXAMPLE 32

(Z) 7-[(6-deoxy-5-C-methyl-4-O-methyl-2,3-O-(1-methylethylidene)-alpha-L-lyxo-hexopyranosyl)oxy]-4-hydroxy-3-(1-hydroxy-2-(2-pyridinyl)ethenyl)-8-methyl-2H-1-benzopyran-2-one 611 mg of pyridylacetic acid hydrochloride and 1.29 mg of 4-dimethylaminopyridine is added to a solution containing 1.452 g of (Z) 7-[(6-deoxy-5-C-methyl-4-O-methyl-2,3-O-(1-methylethylidene)-alpha-L-lyxo-hexopyranosyl)oxy]-4-hydroxy-8-methyl-2H-1-benzopyran-2-one and 15 ml of anhydrous dichloromethane. Then 606 ul of diisopropylcarbodiimide is added. The reaction medium is maintained under agitation for 20 hours. 305.5 mg of pyridylacetic acid hydrochloride and 0.645 mg of 4-dimethylaminopyridine are added. Agitation is again carried out for 12 hours, followed by diluting with 250 ml of dichloromethane, washing with 70 ml of a 1N aqueous solution of sodium dihydrogen phosphate, washing with water, with brine, drying, filtering and evaporating to dryness. 4.06 g of product is obtained which is taken up in the ethyl ether at 0° C. After separating 1.594 g of product is obtained which is purified by chromatography on silica eluting with a $CH_2Cl_2$—MeOH mixture (96.5-3.5). 1.54 g of a product is obtained which is triturated in absolute ethanol and cooled down to −10° C. After separating and drying the mother liquors are concentrated to dryness and 0.317 g of product is obtained which is triturated in 5 ml of ethanol to which 4 ml of sulphuric ether is added. After isolating and drying, 287 mg of sought product is obtained. rf=0.40 $CH_2Cl_2$—$CH_3OH$ (95-5)

EXAMPLE 33

(Z) 7-[(6-deoxy-5-C-methyl-4-O-methyl-alpha-L-lyxo-hexopyranosyl)oxy]-4-hydroxy-3-(1-hydroxy-2-(2-pyridinyl)ethenyl)-8-methyl-2H-1-benzopyran-2-one 1.15 g of the product prepared in the preceding example is added at 0° C. to a solution of trifluoroacetic acid containing 10% water. Agitation is carried out for 4 minutes at 0° C. then 80 ml of buffer solution constituted by 40 ml of 2M $KH_2PO_4$, and 40 ml of 2M $K_2HPO$is added. The precipitate is isolated, followed by taking up in dichloromethane and in tetrahydrofuran, washing with a 10% solution of sodium bicarbonate then with brine and drying. The solvents are evaporated off and 1.09 g of product is collected which is dispersed in 4 ml of absolute ethanol. The insoluble part is isolated by filtration. After rinsing with ethanol and drying 291 mg of sought product is collected.

EXAMPLE 34

(Z) carbamic acid 3'-ester of 7-[(6-deoxy-5-C-methyl-4-O-methyl-alpha-L-lyxo-hexopyranosyl)oxy]-4-hydroxy-3-(1-hydroxy-2-(2-pyridinyl)ethenyl)-8-methyl-2H-1-benzopyran-2-one Stage A: (Z) 7-[(2,3-O-carbonyl-6-deoxy-5-C-methyl-4-O-methyl-alpha-L-lyxo-hexopyranosyl)oxy]-4-hydroxy-3-(1-hydroxy-2-(2-pyridinyl)ethenyl)-8-methyl-2H-1-benzopyran-2-one 84 mg of carbonyldiimidazole is added to a solution containing 210 mg of the product of the preceding example and 10 ml of tetrahydrofuran. The reaction medium is taken to reflux for 1 hour, 40 mg of carbonyldiimidazole is added. Heating under reflux is continued for 1 hour followed by dilution with ethyl acetate, washing with a 1M solution of sodium acid phosphate, then with brine, drying, filtering and concentrating to dryness. After drying 107 mg of sought product is obtained.

Stage B: (Z) carbamic acid 3'-ester of 7-[(6-deoxy-5-C-methyl-4-O-methyl-alpha-L-lyxo-hexopyranosyl)oxy]-4-hydroxy-3-(1-hydroxy-2-(2-pyridinyl)ethenyl)-8-methyl-2H-1-benzopyran-2-one Approximately 15 ml of ammonia is condensed in a flask. 107 mg of the product obtained in Stage A is added. The reaction solution is agitated under reflux of the ammonia for 30 minutes. The ammonia is allowed to escape. The product obtained is poured into 100 ml of tetrahydrofuran in the presence of 50 ml of a 10% aqueous solution of sodium hydrogen sulphate. The organic solution is washed with brine followed by drying, filtering and evaporating to dryness. The product obtained is triturated under ultrasound with isopropyl ether. After separating and drying 89 mg of sought product is obtained.

rf=0.27 $CH_2Cl_2CH_3OH$ (90-10)

NMR of the proton (300 MHz, DMSO-$d_6$, ppm) 1.05 (s, 3H), 1.26 (s, 3H), 2.19 (s, 3H), 3.47 (s, 3H), 3.50 (l, 1H), 4.07 (ws, 1H), 5.15 (dd, 1H, J=3.0 and 10.0 Hz), 5.52 (d, 1H, J=2.5 Hz), 5.60 (ws, 1H), 6.50–6.70 (l, 2H), 6.82 (s, 1H), 7.05 (t, 1H, J=8.0 Hz), 7.09 (d, 1H, J=9.0 Hz), 7.63 (m, 1H), 7.79 (d, 1H, J=9.0 Hz), 7.92 (tl, 1H, J=7.5 Hz), 8.16 (t, 1H, J=6.0 Hz), 13.81 (ws, 1H), 16.0 (ws, 1H).

EXAMPLE 35

5-methyl-1H-pyrrol-2-carboxylic acid 3'-ester of 7-((6-deoxy-5-C-methyl-4-O-methyl-alpha-L-lyxo-hexopyranosyl)oxy]-4-hydroxy-8-methyl-2-oxo-2H-1-benzopyran-3-carboxamide Stage A: 5-methyl-1H-pyrrole-2-carboxylic acid 3'-ester of ethyl 7-[(6-deoxy-5-C-methyl-4-O-methyl-2-O-(tetrahydro-2H-pyran-2-yl)-alpha-L-lyxo-hexopyranosyl)oxy]-8-methyl-2-oxo-4-(phenylmethoxy)-2H-1-benzopyran-3-carboxylate 1.3 ml of 1,2-dihydropyran then 70 mg of paratoluenesulphonic acid are added to a solution containing 4.52 g of the product of Stage A of Example 4. Agitation is carried out for 1 h 30 minutes at ambient temperature, followed by washing with sodium carbonate, drying over magnesium sulphate and filtering. Purification is carried out by chromatography on silica eluting with a hexane-ethyl actetate mixture 7-3. 1.92 g of sought product is obtained. rf=0.38 hexane-ethyl acetate (1-1).

Stage B: 5-methyl-1H-pyrrole-2-carboxylic acid 3'-ester of ethyl 7-[(6-deoxy-5-C-methyl-4-O-methyl-2-O-(tetrahydro-2H-pyran-2-yl)-alpha-L-lyxo-hexopyranosyl)oxy]-4-hydroxy-8-methyl-2-oxo-2H-1-benzopyran-3-carboxylate 200 mg of palladium on carbon is added to a solution containing 1.92 g of the product of Stage A and 25 ml of tetrahydrofuran. Agitation is carried out for 1 hour at ambient temperature under hydrogen pressure. After filtering to eliminate the catalyst, the solvent is evaporated to dryness. The residue is dissolved in the ethyl ether, precipitated with hexane, the solvent is evaporated to dryness followed by drying under reduced pressure. 1.629 g of product is obtained. rf=0.30 hexane-ethyl acetate (1-4).

Stage C: 5-methyl-1H-pyrrol-2-carboxylic acid 3'-ester of 7-((6-deoxy-5-C-methyl-4-O-methyl-alpha-L-lyxo-hexopyranosyl)oxy]-4-hydroxy-8-methyl-2-oxo-2H-1-benzopyran-3-carboxamide A solution of 350 mg of the product of the preceding stage in 10 ml of tetrahydrofuran is saturated with ammonia at 0° C. (by bubbling the ammonia through). The reaction solution is agitated at ambient temperature for 2 days followed by diluting with 50 ml of a hexane-ethyl acetate mixture (1-4), washing with 50 ml of a 100 aqueous solution of sodium hydrogen sulphate, drying and concentrating to dryness. The product obtained (340 mg) is dissolved in 10 ml of methanol and 10 ml of dichloromethane. 50 mg of paratoluenesulphonic acid monohydrate is added. Agitation is carried out for 3 hours at ambient temperature followed by diluting with 70 ml of dichloromethane, washing with a saturated aqueous solution of sodium bicarbonate, drying and concentrating to dryness. After triturating in the presence of isopropyl ether, the insoluble part is separated and 170 mg of sought product is collected.

NMR (300 MHz, DMSO-$d_6$, ppm) 1.07 (s, 3H), 1.30 (s, 3H), 2.23 (s, 3H), 2.24 (s, 3H), 3.47 (s, 3H), 3.66 (d, 1H, J=10 Hz), 4.18 (ws, 1H,), 5.48 (dd, 1H, J=3 and 10 Hz), 5.66 (d, 1H, J=2.5 Hz), 5.74 (ws, 1H), 5.93 (t, 1H, J=3 Hz), 6.78 (t, 1H, J=3 Hz), 7.24 (d, 1H, J=9 Hz), 7.85 (d, 1H, J=9 Hz), 8.73 (ws, 1H H), 8.98 (ws, 1H), 11.66 (ws, 1H), 13.50 (ws, 1H).

EXAMPLE 36

5-methyl-1H-pyrrol-2-carboxylic acid 3'-ester of 3-(cyclopropylcarbonyl) 7-((6-deoxy-5-C-methyl-4-O-methyl-alpha-L-lyxo-hexopyranosyl)oxy]-4-hydroxy-8-methyl-2H-1-benzopyran-2-one 78 µl of cyclopropylcarboxylic acid is added to a solution containing 400 mg of the product of Stage C of Example 1. 173 mg of N-(3-dimethyl-aminopropyl)-N'-ethyl carbodiimide hydrochloride and 306 mg of 4-dimethylaminopyridine in dichloromethane, 78 µl of cyclopropylcarboxylic acid are added. Agitation is carried out for 5 hours at ambient temperature. Another 86 mg of N-(3-dimethylaminopropyl)-N'-ethylcarbodiimide hydrochloride and 159 mg of 4-dimethylaminopyridine are added. Agitation is carried out overnight at ambient temperature followed by diluting with 50 ml of dichloromethane and washing with 50 ml of a 10% aqueous solution of sodium hydrogen sulphate and drying. The solvents are evaporated to dryness. 408 mg of product is obtained (rf=0.78 $CH_2Cl_2$—MeOH 94-6). The product is dissolved in a mixture of 15 Ml of methanol and 10 ml of dichloromethane. 60 mg of paratoluenesulphonic acid is added and agitation is carried out for 3 hours at ambient temperature followed by diluting with dichloromethane, washing with an aqueous solution of sodium bicarbonate, drying over magnesium sulphate and concentrating to dryness. Purification is carried out by chromatography on silica eluting with $CH_2Cl_2$—MeOH (94-6). The product is put into solution in 1 ml of ethyl ether then precipitated by the addition of 5 ml of n-pentane. After separating and drying 139 mg of sought product is obtained.

NMR (300 MHz, DMSO, ppm) 1.07 (s, 3H), 1.30 (s, 3H), 1.24 (ws, 2H), 1.27 (ws, 2H), 2.24 (s, 3H), 2.25 (ws, 3H), 3.48 (S, 3H), 3.58 (m, 1H), 3.66 (d, 1H, J=10 Hz), 4.18 (l, 1H), 5.48 (dd, 1H, J=3 and 10 Hz), 5.68 (d, 1H, J=2.5 Hz), 5.75 (d, 1H, J=5 Hz), 5.93 (t, 1H, J=3 Hz), 6.79 (t, 1H, J=3 Hz), 7.24 (d, 1H, J=9 Hz), 7.91 (d, 1H, J=9 Hz), 11.67 (S, 1H), 13.88 (l, 1H).

EXAMPLE OF PHARMACEUTICAL COMPOSITIONS

Tablets were prepared containing:

Product of Example 4 . . . 150 mg

Excipient s.g.f . . . 1 g

Detail of excipient: starch, talc, magnesium stearate

Product of example 5 . . . 150 mg

Excipient s.q.f. . . . 1 g

Detail of excipient: starch, talc, magnesium stearate

Product of example 2 . . . 150 mg

Excipient s.q.f. . . . 1 g

Detail of excipient: starch, talc, magnesium stearate
Injectable solutions were also prepared from the salts.

PHARMACOLOGICAL STUDY OF THE PRODUCTS OF THE INVENTION

A—Method of Dilutions in Liquid Medium

A series of tubes were prepared in which the same quantity of sterile nutrient medium is distributed. Increasing quantities of the product to be studied is distributed in each tube, then each tube is seeded with a bacterial strain. After incubation for twenty-four hours in a heating chamber at 37° C., the growth inhibition is evaluated by transillumination which allows minimal inhibitory concentrations (M.I.C.) to be determined expressed in micrograms/cm$^3$.

On the following strains:

|  |  |
|---|---|
| S. aureus | 011HT3 |
| S. aureus | 011UC4 |
| S. aureus | 01111T28 |
| S. epidermidis | 012GO20 |
| S. aureus | 011DU5 |
| S. aureus | 011CB20 |
| S. aureus | 011HT26 |
| S. epidermidis | 012GO39 |
| S. epidermidis | 012HI1 |
| Staph. coag. negative | 012HT5 |
| Staph. coag. negative | 014HI1 |
| S. pyogenes | 02A1UC1 |

The following results' were obtained:
0.04<MIC<20

B—Inhibition of Gyrase B

The products are inhibitors of gyrase B; the dose at 50% of DNA supercoiling is less than 5 ug/ml.

What is claimed is:

1. A compound having a formula selected from the group consisting of

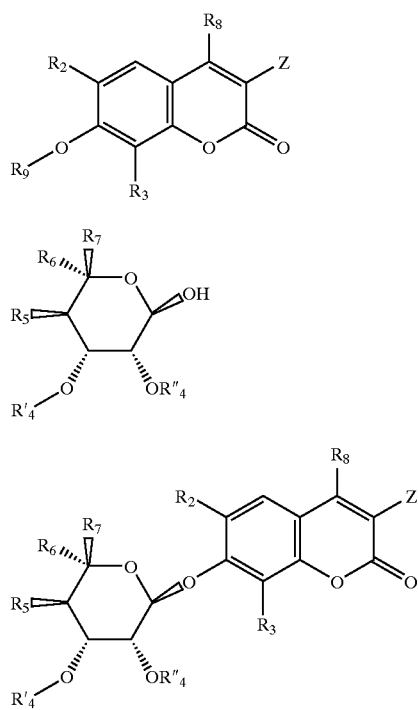

wherein $R_2$ is hydrogen or halogen, $R_3$ is selected from the group consisting of hydrogen, halogen and alkyl of 1 to 8 carbon atoms, $OR'_4$ is a protected —OH, $R''_4$ is hydrogen or $R'_4$ and $R''_4$ together with the carbons to which they are attached form

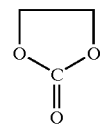

$R_5$ is hydrogen or alkyl of 1 to 4 carbon atoms, $R_6$ is alkyl or —$CH_2$—O-alkyl of up to 8 carbon atoms, $R_7$ is hydrogen or alkyl or 1 to 8 carbon atoms, $R_8$ and $R_9$ are individually —OH or protected —OH, Z is hydrogen or

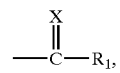

X is selected from the group consisting of =O, =N-Nalk and =NOAlk$_2$, alk and alk$_2$ are individually alkyl of 1 to 12 carbon atoms optionally interrupted by a member of the group consisting of oxygen, sulfur and nitrogen and unsubstituted or substituted by at least one halogen or a group

$R_e$ and $R_f$ are individually hydrogen or alkyl of 1 to 6 carbon atoms or taken with the nitrogen form a heterocycle optionally containing a heteroatom selected from the group consisting of oxygen, sulfur and nitrogen and $R_1$ is selected from the group consisting of a) hydrogen and —OH, b) alkyl, alkenyl and alkynyl of up to 12 carbon atoms optionally interrupted by a member of the group consisting of oxygen, sulfur and nitrogen and unsubstituted or substituted with at least one member of the group consisting of halogen, —OH, —CN, —NO$_2$ and

c) alkoxy of 1 to 8 carbon atoms unsubstituted or substituted with at least one member of the group consisting of halogen, —OH, —CN, —NO$_2$ and

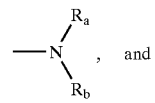

d)

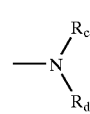

$R_a$ and $R_b$ are individually selected from the group consisting of hydrogen and alkyl of 1 to 8 carbon atoms or taken together with the nitrogen form a heterocycle optionally containing a second heteroatom selected from the group consisting of oxygen, sulfur and nitrogen; $R_c$ and $R_d$ are individually selected from the group consisting of hydrogen and alkyl of 1 to 12 carbon atoms optionally interrupted by a heteroatom selected from the group consisting of oxygen, sulfur and nitrogen and optionally substituted by at least one member of the group consisting of halogen, —OH, —CN$_2$ and —NO$_2$ or taken together with the nitrogen form a heterocycle optionally containing a second heteroatom selected from the group consisting of oxygen, sulfur and nitrogen.

* * * * *